United States Patent
Meers et al.

(10) Patent No.: US 7,491,409 B1
(45) Date of Patent: Feb. 17, 2009

(54) ENCAPSULATION OF BIOACTIVE COMPLEXES IN LIPOSOMES

(75) Inventors: Paul R. Meers, Princeton Junction, NJ (US); Tong Shangguan, Princeton, NJ (US); Donna Cabral-Lilly, Princeton, NJ (US); Patrick Ahl, Princeton, NJ (US); Andrew S. Janoff, Yardley, PA (US)

(73) Assignee: Transave, Inc., Monmouth Junction, NJ (US)

( * ) Notice: Subject to any disclaimer, the term of this patent is extended or adjusted under 35 U.S.C. 154(b) by 0 days.

(21) Appl. No.: 09/914,615

(22) PCT Filed: Mar. 1, 2000

(86) PCT No.: PCT/US00/05395

§ 371 (c)(1),
(2), (4) Date: Dec. 26, 2001

(87) PCT Pub. No.: WO00/51565

PCT Pub. Date: Sep. 8, 2000

Related U.S. Application Data

(60) Provisional application No. 60/122,365, filed on Mar. 2, 1999.

(51) Int. Cl.
*A61K 9/127* (2006.01)
(52) U.S. Cl. .......................... 424/450; 264/4.1; 264/4.3; 264/4.6
(58) Field of Classification Search .................. 424/450, 424/1.21, 9.321, 9.51, 417; 428/402.2; 264/4.1, 264/4.3, 4.6
See application file for complete search history.

(56) References Cited

U.S. PATENT DOCUMENTS

| | | | | |
|---|---|---|---|---|
| 5,286,634 A | * | 2/1994 | Stadler et al. | 435/468 |
| 5,723,147 A | | 3/1998 | Kim et al. | |
| 5,759,573 A | * | 6/1998 | Kim | |
| 5,795,587 A | * | 8/1998 | Gao et al. | 424/450 |
| 6,071,533 A | * | 6/2000 | Papahadjopoulos et al. | 424/450 |

OTHER PUBLICATIONS

Kim, Cancer Research, vol. 53, Apr. 1993, pp. 1596-1598.*
Szoka et al in Proc. Natl. Acad. Sci., USA, vol. 75, #9, pp. 4194-4198, Sep. 1978.*
Fraley et al Biochemistyr, 1981, vol. 20, pp. 6978-6987.*
Ezio et al., "Solubilization and Structural Properties of Nucleic Acids in Reverse Micelles," Controlled Release of Drugs: Polymers and Aggregate Systems, VCH Publishers, Inc., New York (1989), pp. 255-276, XP-001146370.
Ibanez et al., "Spermidine-condensed DNA and cone-shaped lipids improve delivery and expression of exogenous DNA transfer by liposomes," Biochemistry and Cell Biology, 74(5):633-643 (1996).
Luisi et al., "Solubilization of Enzymes and Nucleic Acids in Hydrocarbon Micellar Solutions," Critical Reviews in Biochemistry, 20(4):409-474 (1986).
Tikchonenko et al., "Transfer of condensed viral DNA into Eukaryotic cells using proteoliposomes," Gene, 63(2):321-330 (1988).

* cited by examiner

*Primary Examiner*—Gollamudi Kishore
(74) *Attorney, Agent, or Firm*—Foley Hoag LLP

(57) ABSTRACT

This invention provides a method to prepare liposome-encapsulated bioactive agents such as nucleic acids, comprising complexation of the bioactive agents in reverse micelles prior to forming liposomes, as well as methods of using the liposomes so formed and formulations to deliver nucleic acids to cells.

7 Claims, 23 Drawing Sheets

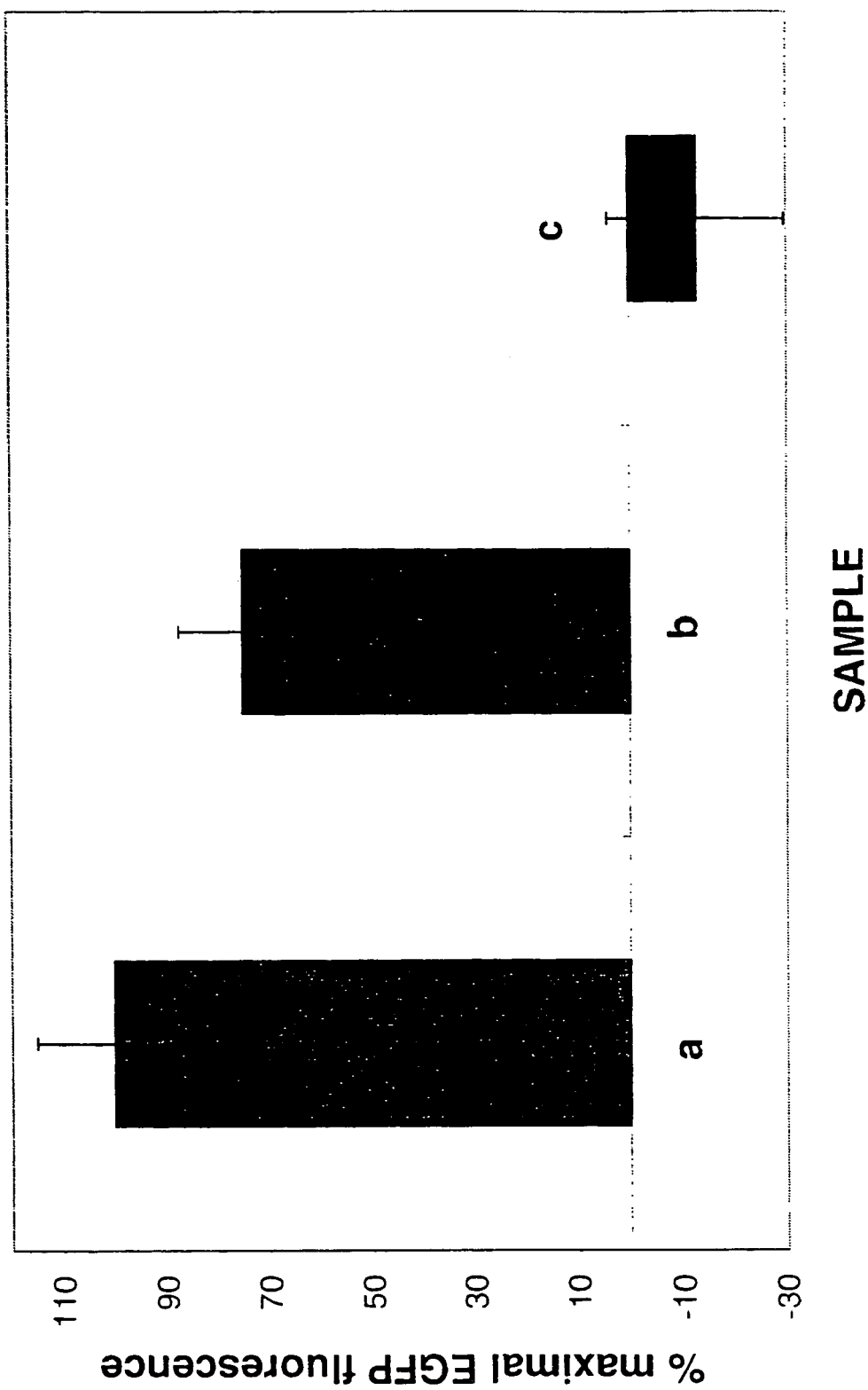

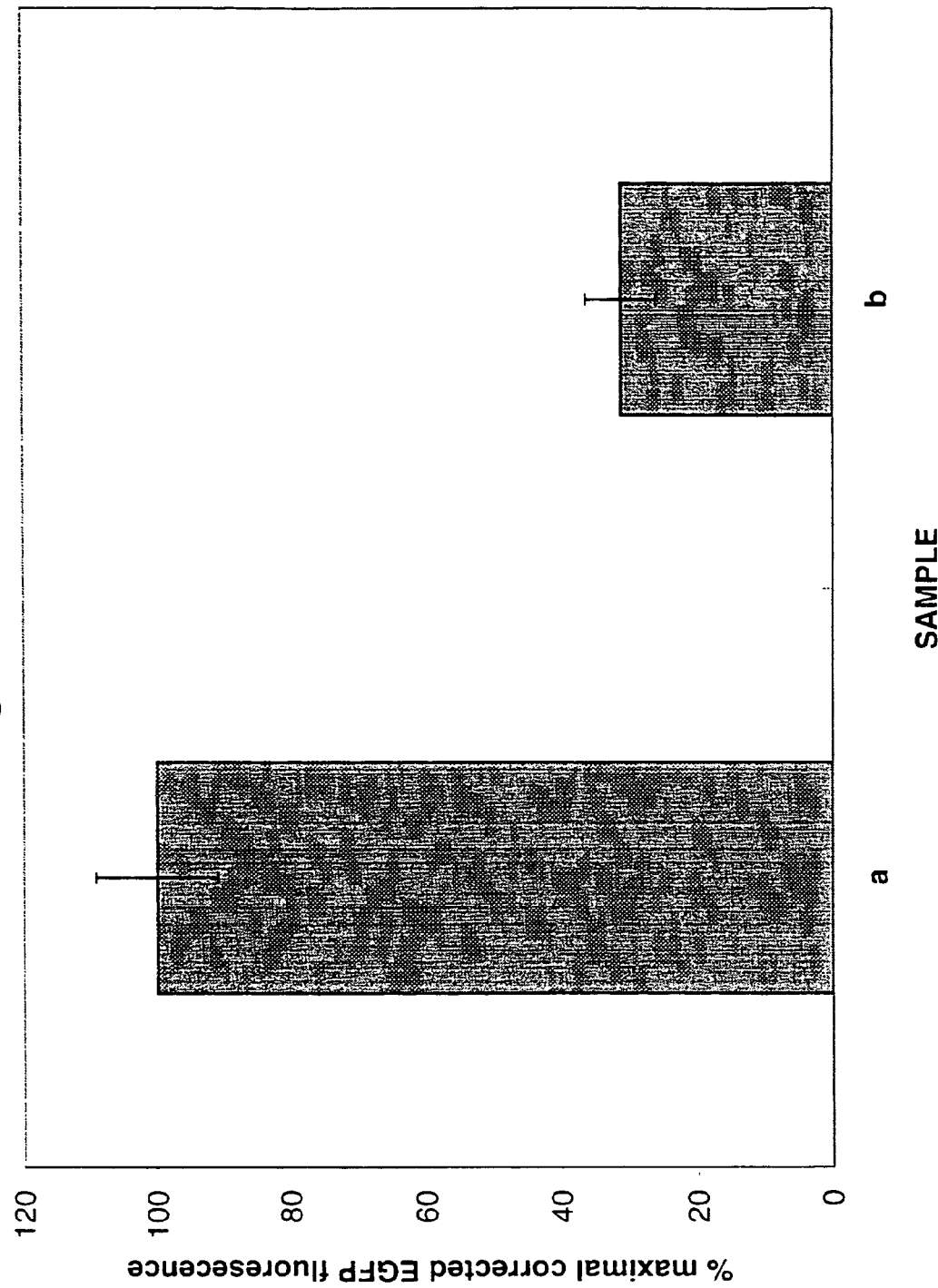

ENCAPSULATION OF BIOACTIVE COMPLEXES IN LIPOSOMES

FIELD OF THE INVENTION

This invention is directed to a method for the encapsulation of complexes, such as polycation-condensed nucleic acids, in liposomes, using an emulsion stabilized by amphipathic lipids as an intermediary within which the complex forms. This invention is also directed to the liposome encapsulated complexes so formed. The method of this invention is applicable for providing liposomes loaded with a variety of compounds which heretofore have been difficult to load into liposomes at high compound to lipid ratios.

BACKGROUND OF THE INVENTION

In order to be useful as pharmaceutical preparations, bioactive agents must be able to reach the therapeutic site in an adequate therapeutic effective amount. While many bioactive agents and drugs are stable in vivo, others are often degraded. When such degradation occurs prior to the drug or bioactive agent reaching its target site, a non-therapeutic amount of drug will reach the target site. Other drugs or bioactive agents are taken up by non-target systems, once again resulting in the lack of a therapeutic amount of a drug or bioactive agent reaching the target site at therapeutically effective amounts. Certain polar drugs can not enter cells at all because of their inability to cross the target cell membrane. The only way that these polar drugs may enter a cell is by uptake by the process of endocytosis, exposing them to degradative lysosomal enzymes in the cell. Yet another problem in the therapeutic delivery of drugs or bioactive agents is the inability to administer a high enough concentration of the drug or bioactive agent to be therapeutic, while avoiding toxicities often associated with some drugs or bioactive agents. These problems have been approached by a number of different methods. When a drug or bioactive agent has no toxicity associated with it, it may be administered in high enough doses to account for degradation, removal by non-target organs and lack of targeting to the site where the therapeutic drug or bioactive agent is required. However, many drugs or bioactive agents are either too expensive to allow such waste or have toxicities that prevent administration of such high dosages. Numerous methods have been used to overcome some of the problems encountered in administering therapeutic amounts of drugs or bioactive agents.

One such method is the encapsulation of drugs or bioactive agents in liposomes. While some drugs or bioactive agents can be encapsulated in liposomes at therapeutically effective doses by passive loading or by gradient loading, these methods are limited either to drugs or bioactive agents with specific chemical properties or to drugs or bioactive agents that can be administered in relatively low concentrations. Some bioactive compounds such as weak bases or weak acids can be loaded remotely into preformed liposomes to form highly concentrated complexes. This type of loading, referred to as remote or gradient loading, requires that the drug or bioactive agent be temporarily able to pass through the lipid bilayer of the liposome. However, this is not the case for all bioactive molecules, many of which cannot pass through the liposomal bilayer.

One area in which attempts to administer therapeutic levels of drugs or bioactive agents have been only partially successful is the area of gene therapy. Gene therapy involves the introduction of an exogenous gene into an appropriate cell type, followed by enablement of the gene's expression within the cell at therapeutically relevant levels. Such therapy has progressed, in a relatively short period of time, from basic research to the introduction into cells of a variety of genes, including those useful for treating cancers (Duque et al., *Histol Histopathol*, 13: 231-242 (1998); Runnebaum et al., *Anticancer Res.*, 17: 2887-2890 (1997)). While naked DNA, in some cases has been taken up into cells (Wolff et al., *Science*, 247: 1465-1468 (1990)), it generally cannot be, due to its large size and high degree of negative charge; moreover, naked DNA cannot be designed so as to be targeted to specific cells. Accordingly, successful gene therapy generally is reliant upon the availability of "vectors" for introducing DNA and other nucleic acids into cells.

Presently, there are two major groups of DNA delivery systems, viral and non-viral. Viral vectors, including replication-deficient viruses, such as retroviruses, adenoviruses, and adeno-associated viruses, have thus far been the most widely described gene delivery vehicles (Robbins et al., *Trends in Biotech*, 16: 3540 (1998)). However, their use has been hampered by the immunogenicity of their viral components, potential risk of reversion to a replication-competent state, potential introduction of tumorgenic mutations, lack of targeting mechanisms, limitations in DNA capacity, difficulty in large scale production and other factors (see, e.g., Lee and Huang, *J Biol Chem*, 271: 8481-8487 (1996)).

Two major types of nonviral vehicles have been developed as alternatives to viral vectors. Cationic liposome-DNA complexes (or "lipoplexes," Feigner et al., *Proc Natl Acad Sci USA*, 84: 7413-7417 (1987)), consisting of cationic lipids and DNA have thus far been the most widely described alternative to viral vectors for gene delivery. However, such lipoplexes suffer from several major drawbacks when used in gene therapy, including low stability, high cytotoxicity, non-biodegradability, poor condensation and protection of DNA, serum sensitivity, large size and lack of tissue specificity. Moreover, as the lipoplexes are positively charged, they generally interact nonspecifically with the negatively charged surfaces of most cells; accordingly, it is generally not possible to target such lipoplexes to specific sites in vivo.

Another variation of lipoplexes and DNA involves polylysine-condensed DNA bound to anionic liposomes (Lee and Huang, *J Biol Chem*, 271: 8481-8487 (1996)). These require certain anionic lipids to form the active structure. The lipoplexes formed either do not completely encapsulate the DNA or must form two or more bilayers around the condensed DNA. In the latter case delivery to the cytoplasm would require the DNA to cross at least three membranes. This would be expected to inhibit transfection efficiency. In the former case, stability may be compromised by exposure of the DNA in physiological salt solutions.

Liposomes are an additional type of nonviral vector alternative, and offer several advantages for such use in comparison to the lipoplexes. For example, liposomal bilayers form around encapsulated nucleic acids, thereby protecting the nucleic acids from degradation by environmental nucleases; lipoplexes, by contrast, do not encapsulate nucleic acids, and hence, cannot completely sequester them away from environmental nucleases. Moreover, liposomes can encapsulate, in their aqueous compartments, other bioactive agents in addition to nucleic acids; lipoplexes, by contrast, cannot because they do not encapsulate aqueous volume. Furthermore, liposomes can be made to be neutrally charged or anionic, as opposed to the restricted ionic nature of the aforementioned lipoplexes. Thus, liposomes can be designed so as to avoid cytotoxicities induced by the delivery vehicle itself and to enhance their accumulation at specific sites of interest.

While the concept of encapsulating bioactive agents in liposomes is not new, many agents have been difficult to encapsulate in liposomes at any level and others have proven difficult to encapsulate in liposomes at levels that would be therapeutically effective. Many small molecules can be encapsulated in liposomes but leak out. Thus, it has also been difficult to encapsulate some bioactive agents and have them retained within the liposomes at a therapeutically effective dose for a therapeutically effective time. For instance, it has been difficult to encapsulate particularly large molecules into a complex within a liposome. It has also been difficult to use many water soluble molecules as therapeutic agents because they are unable to penetrate the cell membrane. When encapsulated stably into liposomes that can fuse to cell membranes, it is possible to deliver these drugs at therapeutically effective doses into the target cells. The method of the present invention enables formation of liposomes containing such drugs or bioactive agents in a therapeutically useful form.

Several attempts have been made to encapsulate nucleic acids in liposomes, these including use of the reverse-phase evaporation (Fraley et al., *J Biol Chem*, 255: 10431-10435 (1980)), dehydration-rehydration (Alizo et al., *J Microencap*, 7: 497-503 (1990)) and freeze-thaw (Monnard et al., *Biochem Biophys Acta*, 1329: 39-50 (1997)) methods of liposome formation. However, each of these methods has several limitations, including requirements for low starting concentrations of nucleic acid, resulting in significant percentages of empty vesicles in the product liposomes, inability to reproducibly encapsulate sufficient quantity of DNA in liposomes to be therapeutically effective at the desired target site and difficulties in optimizing the vehicles for protection of their encapsulated nucleic acids from nuclease-mediated degradation.

Attempts have also been made to complex DNA with complexing agents and subsequently encapsulate the complexed DNA in liposomes. Complexing agents are agents that react with other molecules causing the precipitation or condensation of the molecules. Complexing agents useful in the practice of the present invention are selected from the group consisting of charged molecules that have a charge opposite to the charge on the bioactive agent. The complexing agent may be selected from the group of charged molecules consisting of spermine, spermidine, hexammine cobalt, calcium ions, magnesium ions, polylysines, polyhistidines, protamines, polyanions such as heparin and dextran sulfate, citrate ions, or sulfate ions. For instance, polycations of charge +3 or higher, e.g., polyamines, polylysine and hexammine cobalt (III) are known (see Chattoraj et al., *J Mol Biol*, 121: 327-337 (1978); Gosule L C and Schellman J A. *Nature* 259: 333-335 (1976); Vitello et al., *Gene Therapy*, 3: 396-404 (1996); Widom et al. *J. Mol. Biol.*, 144: 431-453 (1980); Arscott et al., *Biopolymers*, 30: 619-630 (1990); Wilson et al., *Biochem*, 18: 2192-2196 (1979)) to be able to condense DNA molecules, through interaction with multiple negative charges on the DNA. Polyamines, e.g., spermidine (3+) and spermine(4+), have, unlike other types of polycations, been found to occur naturally in all living cells (see, e.g., Ames and Dubin, *J Biol Chem*, 253: 769-775 (1960); Tabor and Tabor, *Annu Rev Biochem*, 53: 749-790 (1984)). High polyamine levels are known to exist in actively proliferating animal cells, and are believed to be essential therein for maintaining normal cell growth (Ames and Dubin, *J Biol Chem*, 253: 769-775 (1960); Tabor and Tabor, *Annu Rev Biochem*, 53: 749-790 (1984); Hafner et al., *J Biol Chem*, 254: 12419-12426 (1979); Pegg, *Biochem J*, 234: 249-262 (1986)).

Liposome encapsulation of spermine-condensed linear DNA in liposomes has been attempted by Tikchonenko et al., *Gene*, 63: 321-330 (1988). However, the starting DNA concentration therein was low, with the consequence that the resulting liposomes also had a low ratio of encapsulated DNA to liposomal lipid (0.02-0.2 micrograms DNA per micromole lipid). Moreover, such condensation of linear DNA molecules in the absence of intermolecular DNA aggregation required control over spermine concentrations to an impracticable degree of precision. Additionally, Baeza et al., *Ori Life Evol Biosphere*, 21: 225-252 (1992) and Ibanez et al., *Biochem Cell Biol*, 74: 633-643 (1996) both report encapsulation of 1-4 micrograms per micromole of spermine-condensed SV40 plasmid DNA in liposomes. However, neither of their preparations were dialyzed against high salt buffers subsequent to liposome formation, the reported amounts of encapsulated DNA actually may include a significant percentage of unencapsulated DNA. Since these liposomal formulations were not exposed to DNAase degradation to determine the percentage of DNA actually sequestered in the liposomes, the high reported amounts probably do not reflect actually encapsulated DNA.

Efficient preparation and use of liposomal encapsulated nucleic acids requires the use of high-concentration suspensions of nucleic acids, in order to minimize the percentage of empty liposomes resulting from the process and to maximize the DNA:liposomal lipid ratios. However, condensation of DNA at high concentrations during known methods of liposome formation generally results in intermolecular aggregation, leading to the formation of nucleic acid-based structures unsuitable for gene delivery. Large aggregates formed by condensation of DNA directly with a complexing agent cannot be easily encapsulated in liposome and such large aggregate structures (on the order of the size of cells) can not efficiently deliver materials to target cells. For instance, if the aggregates are larger than 500 nm, they are rapidly cleared from the circulation because of their size after intravenous administration. On the other hand, larger aggregates may be administered to cells in vitro. However, sometimes the aggregates as too large too be taken up by cells.

Thus, in order to deliver a variety of drugs in therapeutically effective amounts into target cells, it was necessary to provide a method of making liposomes that contain bioactive agents complexed so as to decrease their permeability through the lipid bilayer, while providing a method that also limits the size of the complex to be encapsulated in the liposome so that the resultant therapeutic product is in a therapeutic size range.

SUMMARY OF THE INVENTION

The present invention provides a method of encapsulating a bioactive complex in a liposome which comprises the steps of:

(a) dissolving at least one amphipathic lipid in one or more organic solvents (b) combining at least one aqueous suspension comprising a solution containing a first molecule selected from the group consisting of a bioactive agent and a complexing agent with the lipid-containing organic solution of step (a) so as to form an emulsion in the form of a reverse micelle comprising the first molecule and the lipid;

(c) adding a second aqueous suspension comprising a second molecule selected from the group consisting of a bioactive agent and a complexing agent wherein if the first molecule is a bioactive agent, the second molecule is a complexing agent and vice versa, to the emulsion of step (b), (d) incubating the emulsion of step (c) to allow the complexing agent to contact the bioactive agent thereby forming a complex of the bioactive agent with the complexing agent within lipid stabilized water droplets; wherein said complex is no greater in diameter than the diameter of the droplet and, (e) removing the organic solvent from the suspension of step (d), so as to form liposomes comprising the complexed bioactive agent and the lipid.

The method of the present invention is useful for the preparation of therapeutically useful liposomes containing a wide range of bioactive molecules complexed with complexing agent within the liposome. Preferably, the liposomes are fusogenic liposomes which by the method of the present invention can encapsulate a variety of molecules. These fusogenic liposomes are able to fuse with cell membranes and enable the delivery of bioactive agents in therapeutically effective amounts to cells and organs. In addition, the method of the present invention also allows more than one bioactive agent to be encapsulated in a liposome. One or more bioactive agents may be encapsulated in the same liposomes at the same time by the method of the present invention. If more than one bioactive agent is encapsulated in a liposome by the method of the present invention, it is not necessary for each of the bioactive agents to be in the form of complexes.

Some bioactive agents easily pass through the lipid bilayer and therefore, are not stably sequestered in liposomes. By forming complexes of the bioactive agents with a complexing agent, the bioactive agent remains in the liposomes. A major hurdle has been the problem of encapsulating complexed bioactive agents into liposomes. When the bioactive agent and complexing agent are mixed in solution prior to encapsulation in liposomes, many complexes that are uncontrollably large are formed at the concentrations necessary for efficient loading of liposomes. The term bioactive complex is any bioactive agent bound to a complexing agent such that the complex thus formed results in a change in the physical properties such as decreasing the size of the bioactive molecule, decreasing the solubility of the bioactive agent, precipitating the bioactive agents, condensing the bioactive agent, or increasing the size of the complex. Liposomes that fuse with cell membranes are able to deliver a vast category of molecules to the inside of cells. One advantage of the invention is that, by forming the complex of the bioactive agent in the reverse micelles, the formation of unsuitable large complexes incapable of being encapsulated in therapeutically useful liposomes is prevented.

The formation of complexes comprising a bioactive compound within liposomes has the advantage that such complexes are less likely to leak out of the liposome before delivery to the desired target cell. Furthermore, the formation of a complex can concentrate a large amount of the bioactive agent within the liposome such that the ratio of bioactive agent-to-lipid is high and delivery is efficacious. The disclosed method provides for complexation of bioactive materials with complexing agents within an emulsion followed by encapsulation within a liposome in a manner that prevents the formation of extremely large, detrimental aggregates, greater than several microns, of the bioactive agent and complexing agent.

In one embodiment, the method of the present invention has provided a method to encapsulate nucleic acid complexes. For instance, nucleic acids, such as DNA, are complexed with a condensing agent within reverse (inverted) micelles, followed by formation of liposomes from the micelles. While, as described above, previous attempts have been made to encapsulate DNA in liposomes, none of said methods were successful at efficiently preparing therapeutically useful liposomal DNA.

This invention provides a method to prepare a liposome comprising a condensed nucleic acid, in amounts of at least about 0.5 micrograms nucleic acid per micromole of liposomal lipid.

The liposomes' lipid component preferably comprises a derivatized phospholipid and an additional lipid, generally in proportions of about 20-80 mole % derivatized phospholipid to about 80-20 mole % additional lipid. Preferred derivatized phospholipids include: phosphatidylethanolamine (PE)-biotin conjugates; N-acylated phosphatidylethanolamines (NAPEs), such as N-C12 DOPE; and, peptide-phosphatidylethanolamine conjugates, such as Ala-Ala-Pro-Val DOPE. The additional lipid can be any of the variety of lipids commonly incorporated into liposomes; however, where the derivatized phospholipid is a NAPE, the additional lipid is preferably a phosphatidylcholine (e.g., DOPC). Preferably, the nucleic acid is DNA.

Also provided herein is a method to prepare a pharmaceutical composition comprising the liposome and a pharmaceutically acceptable carrier; said composition can be used to deliver the nucleic acid to the cells of an animal.

Other and further objects, features and advantages will be apparent from the following description of the preferred embodiments of the invention given for the purpose of disclosure when taken in conjunction with the following drawings.

BRIEF DESCRIPTION OF THE DRAWINGS

FIG. 10. Association of transfection activity with the lipid pellet of N-C12-DOPE/DOPC (70:30) prepared with spermine and pEGFP-C1 plasmid DNA (see Example 3); the initial plasmid DNA and spermine solutions contained 200 mM sucrose. After extrusion and dialysis, half of the sample was used for transfection without further handling (a), and the lipid particles from the rest of the sample were pelleted by centrifugation and washed once with HBSS before being used for transfection (b). An N-C12-DOPE/DOPC (70:30) sample with only the 200 mM sucrose was also prepared, and plasmid DNA and spermine were both added externally just before dialysis at an amount equal to that used in the other samples. The pellet of this empty sample (c) was prepared the same way, then, an equal lipid amount of each of the samples was used for transfection under the conditions described in the previous figure legends. After overnight incubation, the cells were labeled with CBAM and the fluorescence of EGFP and calcein blue were measured (error bars are ±s.d).

FIG. 11. Transfection via N-C12 DOPE/DOPC (70:30) liposomes in mouse ascites fluid compared to buffer. Ascites was obtained from the lavage of a tumor-bearing SCID mouse as described in Example 13. Cells were incubated with plasmid DNA-containing liposomes (not a pellet) at a final concentration 10 mM total lipid in HBSS or HBSS with ascites fluid, at a final protein concentration of approximately 3.5 mg/ml (see Example 11). After 3 hr. of incubation, the transfection solution was replaced with serum- and butyrate-containing medium for approximately 20 hr. Expression of EGFP was measured via its fluorescence (error bars are ±s.d).

DETAILED DESCRIPTION OF THE INVENTION

Figure 1A:
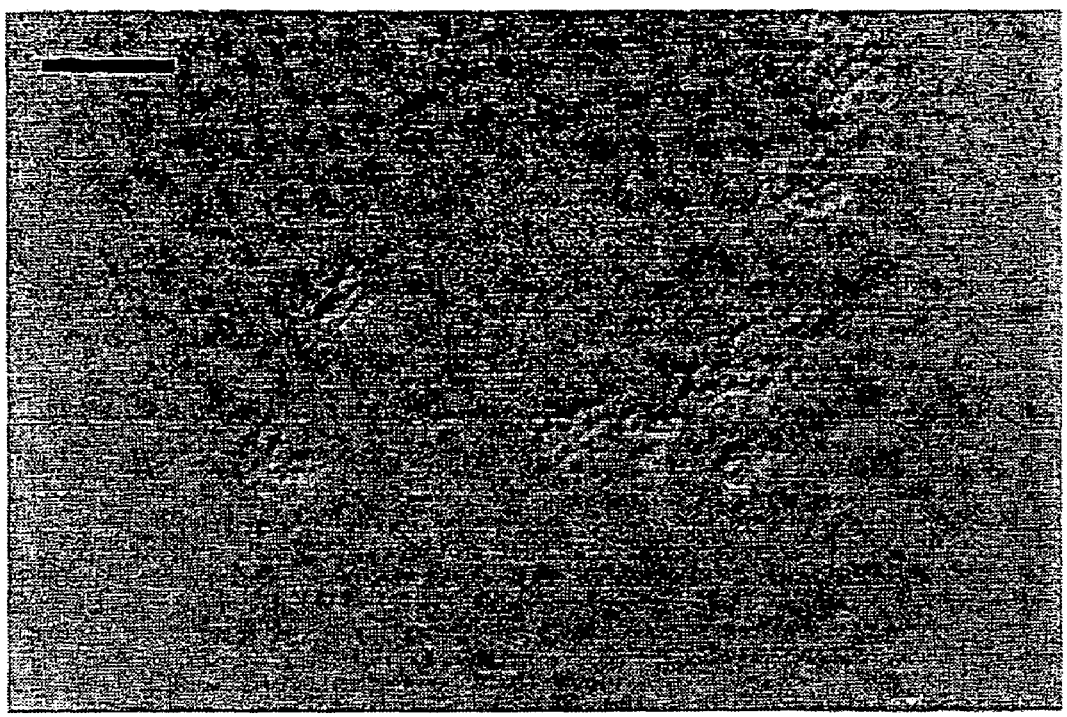
FIG. 1. Micrographs of spermine-mediated plasmid DNA aggregation (200 micrograms plasmid DNA in 125 microliters LSB was mixed gently with 7 mM spermine in 125 microliters LSB). (A) Light microscope observation after 15 minutes incubation at room temperature (bar represents 10 microns). (B) Cryo TEM observation (bar represents 100 nm).

Following are abbreviations, and the corresponding terms, used throughout this application: PE, phosphatidylethanolamine; PC, phosphatidylcholine; EPC, egg phosphatidylcholine; DO-, dioleoyl-; DOPC, dioleoyl phosphatidylcholine; DOPE, dioleoyl phosphatidylethanolamine; NAPE, N-acylated phosphatidylethanolamine; N-C12 DOPE, N-dodecanoyl dioleoyl phosphatidylethanolamine; AAPV-DOPE, Ala-Ala-Pro-Val-dioleoyl phosphatidylethanolamine; CBAM, calcein blue acetoxy methyl ester; PBS, phosphate buffered saline; LSB, low salt buffer; HBSS, Hank's balanced salt solution; EGFP, enhanced green fluorescence protein; SPLV, stable plurilamellar liposomes; MLVs, multilamellar liposomes; ULVs, unilamellar liposomes; LUVs, large unilamellar liposomes; SUVs, small unilamellar liposomes; ds DNA, double stranded DNA; TEM, transmission electron microscopy.

The present invention provides a method of encapsulating a bioactive complex in a liposome which comprises the steps of:
 (a) dissolving at least one amphipathic lipid in one or more organic solvents
 (b) combining at least one aqueous suspension comprising a solution containing a first molecule selected from the group consisting of a bioactive agent and a complexing agent with the lipid-containing organic solution of step (a) so as to form an emulsion in the form of a reverse micelle comprising the first molecule and the lipid;
 (c) adding a second aqueous suspension comprising a second molecule selected from the group consisting of a bioactive agent and a complexing agent wherein if the first molecule is a bioactive agent, the second molecule is a complexing agent or vice versa, to the emulsion of step (b),
 (d) incubating the emulsion of step (c) to allow the complexing agent to contact the bioactive agent thereby forming a complex of the bioactive agent with the complexing agent within lipid stabilized water droplets; wherein said complex is no greater in diameter than the diameter of the droplet and, (e) removing the organic solvent from the suspension of step (d), so as to form liposomes comprising the complexed bioactive agent and the lipid.

The method of the present invention is useful for the preparation of therapeutically useful liposomes containing a wide range of bioactive molecules complexed with complexing agent within the liposome. Preferably, the liposomes are fusogenic liposomes which by the method of the present invention can encapsulate a variety of molecules. These fusogenic liposomes are able to fuse with cell membranes and enable the delivery of bioactive agents in therapeutically effective amounts to cells and organs. In addition, the method of the present invention also allows more than one bioactive agent to be encapsulated in a liposome. One or more bioactive agents may be encapsulated in the same liposomes at the same time by the method of the present invention. If more than one bioactive agent is encapsulated in a liposome by the method of the present invention, it is not necessary for each of the bioactive agents to be in the form of complexes.

The term "Bioactive agents" means any compound or composition of matter that can be administered to animals, preferably humans, for therapeutic or diagnostic purposes. The method of the present invention is useful for encapsulating bioactive agents including but not limited to water-soluble membrane-impermeant agents such as nucleic acids, nucleotide or nucleoside analogs such as cytosine β-D-arabinofuranoside 5'-triphosphate (araCTP), proteins such as cytochrome c, polar anticancer agents such as cisplatin, N-phosphono-acetyl-L-aspartic acid or 5-fluoroorotic acid, polar or charged derivatives of anticancer agents, polar peptides, histone deacetylase inhibitors such as butyrate, etc. Bioactive agents also include, but are not limited to, agents selected from the group consisting of nucleic acids such as DNA and RNA, antiviral agents such as acyclovir, zidovudine and the interferons; antibacterial agents such as aminoglycosides, cephalosporins and tetracyclines; antifungal agents such as polyene antibiotics, imidazoles and triazoles; antimetabolic agents such as folic acid, and purine and pyrimidine analogs; antineoplastic agents such as the anthracycline antibiotics and plant alkaloids; carbohydrates, e.g., sugars and starches; amino acids, peptides, proteins such as cell receptor proteins, immunoglobulins, enzymes, hormones, neurotransmitters and glycoproteins; dyes; radiolabels such as radioisotopes and radioisotope-labeled compounds; radiopaque compounds; fluorescent compounds; mydriatic compounds; bronchodilators; local anesthetics; and the like.

The term bioactive complex is any bioactive agent bound to a complexing agent such that the complex thus formed results in a change in the physical properties such as decreasing the size of the bioactive molecule, decreasing the solubility of the bioactive agent, precipitating the bioactive agents, condensing the bioactive agent, or increasing the size of the complex.

Water-in-oil emulsions containing reverse micelles have been used previously to study enzyme kinetics (e.g. Bru et al., *Biochem J*, 310: 721-739 (1995)) and to form liposomes (e.g. Szoka et al., *Proc Nat Acad Sci USA*, 75: 4194-4198 (1978); Gruner et al., *Biochem*, 24: 2833-2842 (1984)), but the use of such emulsions to modulate complexation of two compounds for the purpose of loading liposomes has not been previously reported.

Emulsions can be formed by various methodologies, well within the purview of ordinarily skilled artisans. Sonication, vortexing, mechanical stirring, static mixing, homogenization, injection, microfluidization, colloid mills, pressure emulsifiers and/or Kady mills can be used to prepare emulsions of various types including various orders of addition of materials. The emulsions of the present invention are formed in two steps so that at least one component, the bioactive agent or the complexing agent is pre-sequestered within the water droplets of the lipid-stabilized emulsion before addition of the aqueous dispersion of the other agent.

Upon removal of solvent from the lipid-stabilized emulsion, "liposomes" are formed. Solvent can be removed by any number of methods including but not limited to rotary evaporation and streaming of nitrogen.

"Liposomes" are self-assembling structures comprising one or more lipid bilayers, each of which comprises two monolayers containing amphipathic lipid molecules oppositely oriented. Amphipathic lipids comprise a polar (hydrophilic) headgroup region covalently linked to one or two non-polar (hydrophobic) acyl chains. Energetically unfavorable contacts between the hydrophobic acyl chains and the surrounding aqueous medium induce the amphipathic lipid molecules to arrange themselves such that their polar headgroups are oriented towards the bilayer's surface, while the acyl chains reorient towards the interior of the bilayer. An energetically stable structure is thus formed in which the acyl chains are effectively shielded from coming into contact with the aqueous environment.

Liposomes (see, e.g., Cullis et al., *Biochim. Biophys Acta*, 559: 399-420 (1987); New, 1995) can have a single lipid bilayer (unilamellar liposomes, "ULVs"), or multiple lipid bilayers (multilamellar liposomes, "MLVs" or "SPLVs"). Each bilayer surrounds, or encapsulates, an aqueous compartment. Given this encapsulation of aqueous volume within a protective barrier of lipid molecules, liposomes are able to sequester encapsulated molecules, e.g., nucleic acids, away from the degradative effects of factors, e.g., nuclease enzymes, present in the external environment. Such protection of encapsulated content is, in the case of nucleic acid molecules, demonstrated, for example, by the type of agarose gel analysis set forth in Example 9, the results of which are presented in FIG. 4.

Liposomes can have a variety of sizes, e.g., an average diameter as low as 25 nm or as high as 10,000 nm or more. Size is affected by a number of factors, e.g., lipid composition and method of preparation, well within the purview of ordinarily skilled artisans to determine and account for, and is determined by a number of techniques, such as quasi-elastic light scattering, also within the artisans' purview.

Various methodologies, also well within the purview of ordinarily skilled artisans, such as sonication, homogenization, French Press application and milling can be used to prepare liposomes of a smaller size from larger liposomes. Extrusion (see, e.g., U.S. Pat. No. 5,008,050) can be used to size reduce liposomes, that is to produce liposomes having a predetermined mean size by forcing the liposomes, under pressure, through filter pores of a defined, selected size. Tangential flow filtration (WO89/008846), can also be used to regularize the size of liposomes, that is, to produce a population of liposomes having less size heterogeneity, and a more homogeneous, defined size distribution. The contents of these documents are incorporated herein by reference.

Liposomes of this invention can be unilamellar, or oligolamellar, and can have a size equal to that of liposomes produced by any of the methods set forth hereinabove. However, in preferred embodiments of this invention, the liposomes are unilamellar liposomes having number average sizes of about 50-300 nm.

Liposomes are composed of a variety of lipids, both amphipathic and nonamphipathic, obtained from a variety of sources, both natural and synthetic. Suitable liposomal lipids include, without limitation, phospholipids such as phosphatidylcholines ("PC's"), phosphatidylethanolamines ("PE's"), phosphatidylserines ("PS's"), phosphatidylglycerols ("PG's"), phosphatidylinositols ("PI's") and phosphatidic acids ("PA's"). Such phospholipids generally have two acyl chains, these being either both saturated, both unsaturated or one saturated and one unsaturated; said chains include, without limitation: myristate, palmitate, stearate, oleate, linoleate, linolenate, arachidate, arachidonate, behenate and lignocerate chains.

Phospholipids can also be derivatized, by the attachment thereto of a suitable reactive group. Such a group is generally an amino group, and hence, derivatized phospholipids are typically phosphatidylethanolamines. The different moieties suited to attachment to PE's include, without limitation: acyl chains (WO98/16199), useful for enhancing the fusability of liposomes to biological membranes; peptides (WO98/16240), useful for destabilizing liposomes in the vicinity of target cells; biotin and maleimido moieties (U.S. Pat. Nos. 5,059,421 and 5,399,331, respectively), useful for linking targeting moieties such as antibodies to liposomes; and, various molecules such as gangliosides, polyalkylethers, polyethylene glycols and organic dicarboxylic acids (see, e.g., U.S. Pat. Nos. 5,013,556, 4,920,016 and 4,837,028). The contents of the above-cited documents are incorporated herein by reference.

Accordingly, in the most preferred embodiments of this invention, the liposomes prepared by the method of the present invention comprise a derivatized phospholipid, adapted so as to enhance delivery of their contents. The liposomes may also, but are not required to, comprise additional lipids as well, said additional lipids being incorporated into the liposomes for a number of reasons apparent to artisans of ordinary skill in the field of liposomology. Such reasons include, without limitation, stabilizing or targeting the liposomes, as well as further altering the liposomes' pharmacokinetic behavior. Suitable additional lipids include any of those lipids commonly recognized as suitable for incorporation in liposomes, including, without limitation, phospholipids, glycolipids and sterols.

Preferably, liposomes of this invention have a lipid component which comprises a derivatized phospholipid and an additional lipid. The derivatized phospholipid has the formula:

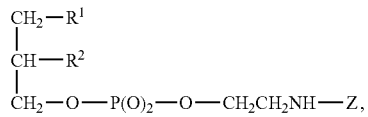

wherein: Z is selected from the group consisting of biotin, a maleimide moiety, a group designated $R^3$ and a group having the formula X-Y; X is a linker selected from the group consisting of a single bond and the group $R^4$; and, Y is an enzyme cleavable peptide comprising an amino acid sequence which is the substrate of a cell-secreted peptidase. Each of $R^1$, $R^2$, $R^3$ and $R^4$ is a group having the formula $-OC(O)(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}CH_3$, wherein: n1 is zero or an integer of from 1 to 22; n3 is zero or an integer of from 1 to 19; n5 is zero or an integer of from 1 to 16; n7 is zero or an integer of from 1 to 13; n9 is zero or an integer of from 1 to 10; and, each of n2, n4, n6 and n8 is zero or 1. Each of n1, n2, n3, n4, n5, n6, n7, n8 and n9 is the same or different at each occurrence.

For $R^1$ and $R^2$, the sum of $n1+2n2+n3+2n4+n5+2n6+n7+2n8+n9$ is independently an integer of from 12 to 22, whereas for $R^3$ and $R^4$, the sum of $n1+2n2+n3+2n4+n5+2n6+n7+2n8+n9$ is independently an integer of from 2 to 22. Said derivatized phospholipid preferably comprises about 20 to 80 mole percent of the liposomal lipid.

Where $R^3$ is $-C(O)(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}CH_3$, the derivatized phospholipid is an N-acylated phosphatidylethanolamine ("NAPE," see WO98/16199). Preferably, $R^3$ is then $-OC(O)(CH_2)_{n1}CH_3$, more preferably $-OC(O)(CH_2)_{10}CH_3$.

Preferably, the derivatized phospholipid is an N-acylated PE. Such NAPEs are useful in preparing fusogenic liposomes and are preferred for preparing liposomes comprising the drug or bioactive agent complexes of the present invention.

NAPE-induced bilayer destabilization induces the bilayers to fuse to biological membranes in the vicinity and hence, enhances the bilayers' fusogenicity (Shangguan et al., Biochim Biophys Acta, 1368: 171-183 (1998)). Enhanced fusogenicity, in turn, can be used to deliver encapsulated bioactive agents, such as nucleic acids or other agents that can not cross the cell membrane, to cells, by combining the cells with the liposomes under conditions, e.g., the presence of appropriate concentrations such as $Ca^{2+}$ and $Mg^{2+}$. Liposome-cell contact results in release of the liposome-encapsulated bioactive agents local to the cells, and/or directly into the cells' cytoplasm as a result of fusion between liposome and cell membranes. Such delivery is either in vivo or in vitro.

Where $R^3$ is the acyl chain or the peptide, and hence, where the derivatized phospholipid is a NAPE or peptide-lipid conjugate, at least one of $R^1$ and $R^2$ is preferably an unsaturated acyl chain, i.e., at least one of n2, n4, n6 and n8 therein is equal to 1. Unsaturated acyl chains include, without limitation, palmitoleate, oleate, linoleate, linolenate, and arachidonate chains. Preferably, the unsaturated acyl chain is an oleate chain ("$-OC(O)(CH_2)_7CH=CH(CH_2)_7CH_3$"). More preferably, both $R^1$ and $R^2$ are oleate chains, i.e., the derivatized phospholipid then is:

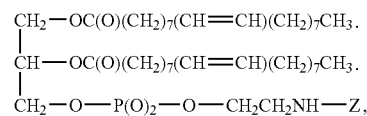

wherein Z is $R^3$ or X-Y. Most preferably, the derivatized phospholipid is then:

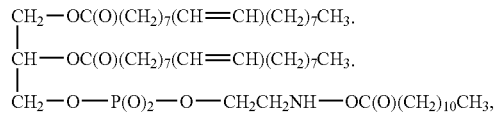

i.e., "N-C12 DOPE".

Where the derivatized phospholipid is N-C12 DOPE, the liposomal lipid preferably also comprises a phosphatidylcholine, preferably a PC having at least one unsaturated acyl chain, and most preferably dioleoyl phosphatidylcholine. Preferably, the liposomal lipid comprises about 70 mole % N-C12 DOPE and about 30 mole % DOPC (i.e., is a "70:30" formulation of N-C12 DOPE and DOPC, wherein liposomal lipid concentrations are referred to herein by ratio, and wherein such ratios are an indication of the relative percentages in the liposomal lipid of the particular lipids referred to).

The liposomal lipid can also comprise a "headgroup-modified lipid," i.e., a lipid having a polar group derivatized by the attachment thereto of a moiety capable of inhibiting the binding of serum proteins to a liposome incorporating the lipid. Incorporation of headgroup-modified lipids into liposomes thus alters their pharmacokinetic behavior, such that the liposomes remain in the circulation of an animal for a longer period of time then would otherwise be the case (see, e.g., Blume et al., *Biochim. Biophys. Acta.*, 1149:180 (1993); Gabizon et al., *Pharm. Res.*, 10(5):703 (1993); Park et al., *Biochim. Biophys Acta.*, 257: 1108 (1992); Woodle et al., U.S. Pat. No. 5,013,556; Allen et al., U.S. Pat. Nos. 4,837,028 and 4,920,016; the contents of these documents being incorporated herein by reference).

Headgroup-modified lipids are typically phosphatidylethanolamines (PE's), for example dipalmitoyl phosphatidylethanolamine ("DPPE"), palmitoyloleoyl phosphatidylethanolamine ("POPE") and dioleoyl phosphatidylethanolamine ("DOPE"), amongst others. Such lipids have headgroups generally derivatized with a polyethylene glycol, or with an organic dicarboxylic acid, such as succinic or glutaric acid ("GA"), or their corresponding anhydrides. The amount of the headgroup-modified lipid incorporated into the lipid carrier generally depends upon a number of factors well known to the ordinarily skilled artisan, or within his purview to determine without undue experimentation. These include, but are not limited to: the type of lipid and the type of headgroup modification; the type and size of the carrier; and the intended therapeutic use of the formulation. Typically, from about 5 mole percent to about 20 mole percent of the lipid in a headgroup-modified lipid-containing lipid carrier is headgroup-modified lipid.

Complexing agents generally including but are not limited to a group oppositely charged to the bioactive agent including spermine, spermidine, cobalt hexamine, calcium ions, magnesium ions, polylysines, polyhistidines, protamines, polyanions such as heparin and dextran sulfate, citrate ions and sulfate ions. One of skill in the art will also recognize other useful complexing agents useful in the method of the present invention.

Condensed nucleic acids encapsulated in the liposome are DNA, including genomic DNA, plasmid DNA and cDNA, or RNA; preferably, the encapsulated nucleic acid is DNA, more preferably, closed (circular) plasmid DNA. Condensed nucleic acids are encapsulated in the liposomes at a level of at least about 0.5 micrograms per micromole liposomal lipid, or at least about 0.75, 1.0, 1.25, 1.5, 1.75 or 2 micrograms per micromole. More preferably, the liposomes contain about 2 micrograms nucleic acid per micromole lipid to about 20 micrograms per micromole. "Condensed" as used herein in connection with nucleic acids refers to nucleic acids which have been combined with one or more polycations such that the nucleic acid strands are more tightly packed than would be the case in the absence of the polycations. Such packing allows nucleic acids to be encapsulated in liposomes, yet leaves the nucleic acids in a transfectable, transcription-ready conformation.

Accordingly, in preferred embodiments of this invention, the method prepares liposomes comprising a condensed DNA and liposomal lipid which comprises about 70 mole % N-C12 DOPE and about 30 mole % DOPC. Such liposomes contain at least about 0.5 micrograms condensed DNA per micromole of lipid.

Liposomes provided by the method of the present invention can contain one or more bioactive agents in addition to the complexed bioactive agent. Bioactive agents which may be associated with liposomes include, but are not limited to: antiviral agents such as acyclovir, zidovudine and the interferons; antibacterial agents such as aminoglycosides, cephalosporins and tetracyclines; antifungal agents such as polyene antibiotics, imidazoles and triazoles; antimetabolic agents such as folic acid, and purine and pyrimidine analogs; antineoplastic agents such as the anthracycline antibiotics and plant alkaloids; sterols such as cholesterol; carbohydrates, e.g., sugars and starches; amino acids, peptides, proteins such as cell receptor proteins, immunoglobulins, enzymes, hormones, neurotransmitters and glycoproteins; dyes; radiolabels such as radioisotopes and radioisotope-labeled compounds; radiopaque compounds; fluorescent compounds; mydriatic compounds; bronchodilators; local anesthetics; and the like.

Liposomal bioactive agent formulations can enhance the therapeutic index of the bioactive agent, for example by buffering the agent's toxicity. Liposomes can also reduce the rate at which a bioactive agent is cleared from the circulation of animals. Accordingly, liposomal formulation of bioactive agents can mean that less of the agent need be administered to achieve the desired effect.

The liposome of this invention can be dehydrated, stored and then reconstituted such that a substantial portion of their internal contents are retained. Liposomal dehydration generally requires use of a hydrophilic drying protectant such as a disaccharide sugar at both the inside and outside surfaces of the liposomes' bilayers (see U.S. Pat. No. 4,880,635, the contents of which are incorporated herein by reference). This hydrophilic compound is generally believed to prevent the rearrangement of the lipids in liposomes, so that their size and contents are maintained during the drying procedure, and through subsequent rehydration. Appropriate qualities for such drying protectants are that they be strong hydrogen bond acceptors, and possess stereochemical features that preserve the intermolecular spacing of the liposome bilayer components. Alternatively, the drying protectant can be omitted if the liposome preparation is not frozen prior to dehydration, and sufficient water remains in the preparation subsequent to dehydration.

Also provided herein is a pharmaceutical composition comprising a pharmaceutically acceptable carrier and the liposome of this invention. Said composition is useful, for example, in the delivery of nucleic acids to the cells of an animal. "Pharmaceutically acceptable carriers" as used herein are those media generally acceptable for use in connection with the administration of lipids and liposomes, including liposomal bioactive agent formulations, to animals, including humans. Pharmaceutically acceptable carriers are generally formulated according to a number of factors well within the purview of the ordinarily skilled artisan to determine and account for, including without limitation: the particular liposomal bioactive agent used, its concentration, stability and intended bioavailability; the disease, disorder or condition being treated with the liposomal composition; the subject, its age, size and general condition; and the composition's intended route of administration, e.g., nasal, oral, ophthalmic, topical, transdermal, vaginal, subcutaneous, intramammary, intraperitoneal, intravenous, or intramuscular (see, for example, Nairn (1985), the contents of which are incorporated herein by reference). Typical pharmaceutically acceptable carriers used in parenteral bioactive agent administration include, for example, D5W, an aqueous solution containing 5% weight by volume of dextrose, and physiological saline. Pharmaceutically acceptable carriers can contain additional ingredients, for example those which enhance the stability of the active ingredients included, such as preservatives and anti-oxidants.

Further provided herein is a method of encapsulating a nucleic acid, e.g., DNA, in a liposome which comprises the steps of: (a) combining an aqueous suspension of the nucleic acid with an organic solution comprising a lipid, e.g., a derivatized phospholipid and an additional lipid, so as to form a suspension of reverse (inverted) micelles comprising the nucleic acid and the lipid; (b) adding a polycation to the micellar suspension, so as to condense the nucleic acid within the reverse micelles; and, (c) removing the organic solvent from the suspension of step (b), so as to form liposomes comprising the nucleic acid and the lipid from the reverse micelles. The ratio of nucleic acid to liposomal lipid achieved by the encapsulation method is at least about 0.5 micrograms nucleic acid per micromole lipid.

Lipids useful in the practice of this invention are, as described hereinabove, those lipids recognized as suitable for incorporation in liposomes, either on their own or in connection with additional lipids; these include, phospholipids, glycolipids, sterols and their derivatives. Organic solvents used in this method are any of the variety of solvents useful in dissolving lipids during the course of liposome preparation; these include, without limitation, methanol, ethanol, dimethylsulfoxide, chloroform, and mixtures thereof. Preferably, the organic solvent is chloroform.

Polycations useful in the method of the present invention to condense nucleic acids are any of the chemical compounds having three or more ionizable groups which can be used to condense nucleic acids, other bioactive agents or drugs; these include, without limitation, polylysine, polyamines (e.g., spermine and spermidine), hexammine cobalt (III), polyhistidine, polyethyleneimine and the like. Preferably, the polycation is spermine. Nucleic acids useful in the practice of this invention include, DNA, e.g., genomic DNA, cDNA and plasmid DNA, linear or closed, as well as RNA. Nucleic acids are suspended in aqueous media by commonly understood, and readily practiced, methods; e.g., vortexing, of suspending macromolecules. Suitable aqueous media are aqueous solutions of various additives, such as buffering agents, and are substantially free of certain ingredients, such as salts and nuclease enzymes.; such media include, without limitation low salt buffer ("LSB," see Example 3 hereinbelow).

Water-in-oil emulsions stabilized by phospholipids contain reverse micelles. Reverse micelles (see Bru et al., *Biochem J*, 310: 721-739 (1995)) are amphipathic lipid-based structures in which the lipids' hydrophilic domains are sequestered inside the micelles' surfaces, while the lipids' hydrophobic domains are arrayed around the exterior.

Figure 2:
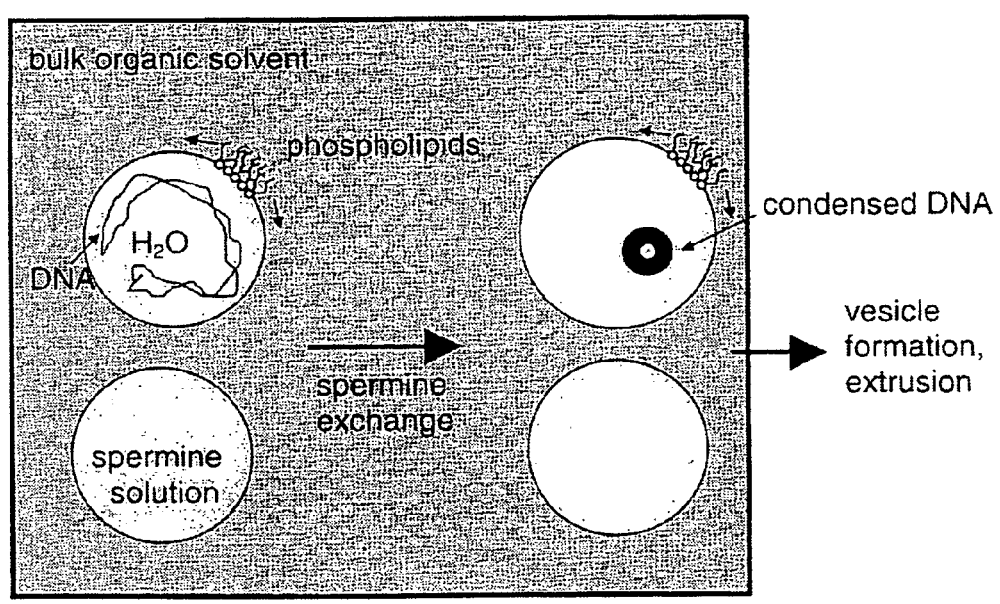
FIG. 2. Schematic representation of method of DNA encapsulation. Condensation of DNA occurs (I) within phospholipid-stabilized water droplets that have formed around the DNA in a bulk organic solvent. Separate spermine-containing droplets transfer (II) spermine into the DNA containing droplets by transient (III) contact and exchange. After condensation within the emulsion (IV), vesicles are formed by solvent evaporation and further extruded to smaller sizes (V).

Emulsions with reverse micelles are formed, as described above and in FIG. 2 hereinbelow, shield bioactive agents including nucleic acids sequestered therein from the intermolecular contacts which would otherwise lead to their aggregation in the presence of complexing agent and unsuitability for incorporation into liposomes. Said process is conducted so as to maximize the percentage of the resulting liposomes containing the desired complexes.

Within the emulsion, complexes are formed by way of the exchange of added complexing agents, such as polycations, or bioactive agents between the aqueous compartment of the reverse micelles in the emulsion (see, e.g., Bru et al., *FEBS*, 282: 170-174 (1991); Fletcher et al., *J Chem Soc Faraday Trans I*, 83: 985-1006 (1987)). In the case of encapsulation of DNA complexes, suitable polycations are any of those polycations useful to condense nucleic acids. For example, spermine and spermidine have both been used (see, e.g., Chattoraj et al., *J Mol Biol*, 121: 327-337 (1978) and Gosule et al., *Nature*, 259: 333-335 (1976), the contents of which are incorporated herein by reference), in vitro to condense individual plasmids, but only at low DNA concentrations, in order to avoid aggregation of the condensed plasmids. Such concentrations were minimal enough that, had liposome encapsulation of the condensed nucleic acids been attempted, there would have been a significant number of empty, i.e., non-DNA containing, liposomes. Polylysine and hexamine cobalt (III) are also available for nucleic acid condensation.

Concentrations of polycations suitable for condensing nucleic acids are those concentrations which result in the neutralization of a sufficient number of nucleic acid negative charges, e.g., about 90% or more of the negative charges in the case of DNA (Wilson et al., *Biochem*, 18: 2192-2196 (1979)). Ordinarily skilled artisans are well able to determine suitable or optimal polycation concentrations given the nucleic acid to be condensed, the polycation used, nucleic acid concentrations and polycation valency.

Moreover, additional factors well within the purview of ordinarily skilled artisans to determine and account for can affect the concentrations of polycations suitable for condensation of bioactive agents such as nucleic acids. For example, NAPEs such as N-C12 DOPE bear a net negative charge, by way of the additional acyl chain; hence, such lipids can interact with positively charged molecules, thereby diminishing the pool of polycations available for nucleic acid condensation.

Accordingly, in such cases, it may be necessary to add an amount of polycation above that otherwise required for nucleic acid condensation. Such sufficient additional amounts of polycations can be determined by a number of means, including, for example, the type of partitioning experiments set forth in Example 4. Such experiments provide data (see FIG. 3) showing the additional polycation concentrations required for nucleic acid condensation. For example, with the concentrations of nucleic acid and lipid used in Example 3, 0.6 mM spermine was sufficient for plasmid DNA condensation, but this amount increased to 0.85 mM in the presence of the NAPE N-C12 DOPE, in the concentration set forth. However, polycation concentrations greater than these, i.e., greater than minimally necessary, can be used—for instance, again looking to the conditions of Example 3 as exemplary, a final spermine concentration of 8-20 mM in the emulsion was found to be optimal for nucleic acid and lipid charge neutralization.

Ordinarily skilled artisans are well able to determine lipid and nucleic acid concentrations suitable for the practice of this invention. For example (see Example 3, hereinbelow), in order to encapsulate condensed plasmid DNA within 200 nm spherical liposomes, 200 micrograms of pZeoLacZ plasmid DNA in 125 microliters of LSB were combined with 30 micromoles of a 70:30 mole ratio combination of N-C12 DOPE and DOPC.

Accordingly, preferred embodiments of this invention are practiced with a condensed nucleic acid which is plasmid DNA, a lipid comprising a derivatized phospholipid, e.g., N-C12 DOPE, chloroform and spermine, e.g., at a concentration of about 1 mM or greater.

Still further provided herein is a method of transfecting the cells of an animal with a bioactive agent such as a nucleic acid, said method comprising the step of contacting the cells with a liposome of this invention containing the complexed nucleic acid. Such contact is either in vitro, in which case, a composition comprising the liposome is added to the culture medium surrounding the cells, or in vivo, in which case the liposome is administered in a pharmaceutical composition also comprising a pharmaceutically acceptable carrier, and is administered to the animal by any of the standard means of administering such compositions to animals.

In vivo contact, especially where specificity or targeting is desired, is aided by incorporating in the liposome a means of either directing the liposome to a specific site, e.g., by conjugating an antibody to the liposomes via streptavidin, causing the liposome's contents to be preferentially released at a certain site, e.g., by the incorporation of NAPEs or peptide-lipid conjugates into the liposomes, and/or by causing the liposomes to accumulate at sites, e.g., tumors by incorporating therein a headgroup-modified lipid.

Transfection success can be detected, for example, where the plasmid pEGFP-1 contains a DNA sequence encoding the enhanced green fluorescence protein, whose presence is detected by fluorescence microscopy. Accordingly, successful transfection of cells with this plasmid (see Examples 10-12) is readily determined by assessing the quantity of fluorescence exhibited by the cells. Results of these experiments (see FIGS. 8-12) demonstrate both the successful transfection of OVCAR-3 cells with the pEGFP-1_plasmid, as well as the high level of expression of the transfected plasmid in a significant percentage of the transfected cells.

Figure 8A:
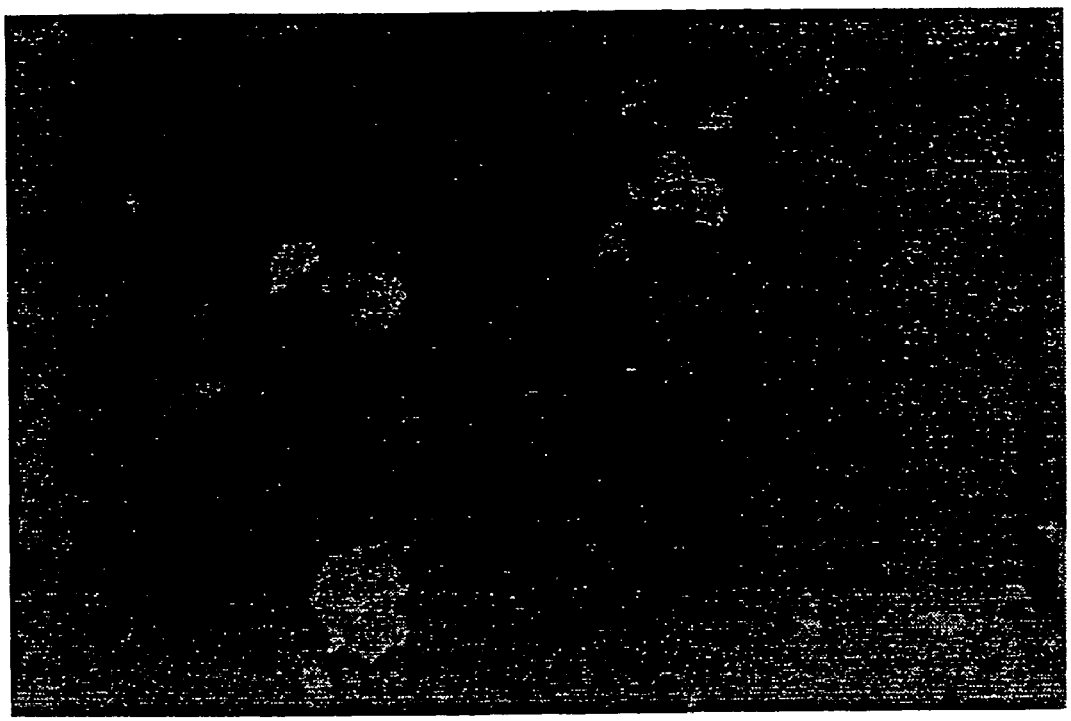
FIG. 8. Fluorescence photomicrographs of confluent OVCAR3 cells after transfection (see Example 11) with the N-C12 DOPE/DOPC (70:30) preparations. Liposomal samples were prepared (see Example 3) with pEGFP-C1 plasmid DNA (a) with spermine or (b) without spermine; a sample (c) of empty N-C12 DOPE/DOPC (70:30) liposomes without spermine plus free pEGFP-C1 plasmid DNA added outside the preformed liposomes was also tested. The amount of plasmid DNA added to the empty liposomes in sample c was equal to the total amount in each of the other preparations. Equal liposome concentrations were used in the experiments.
Figure 8B:
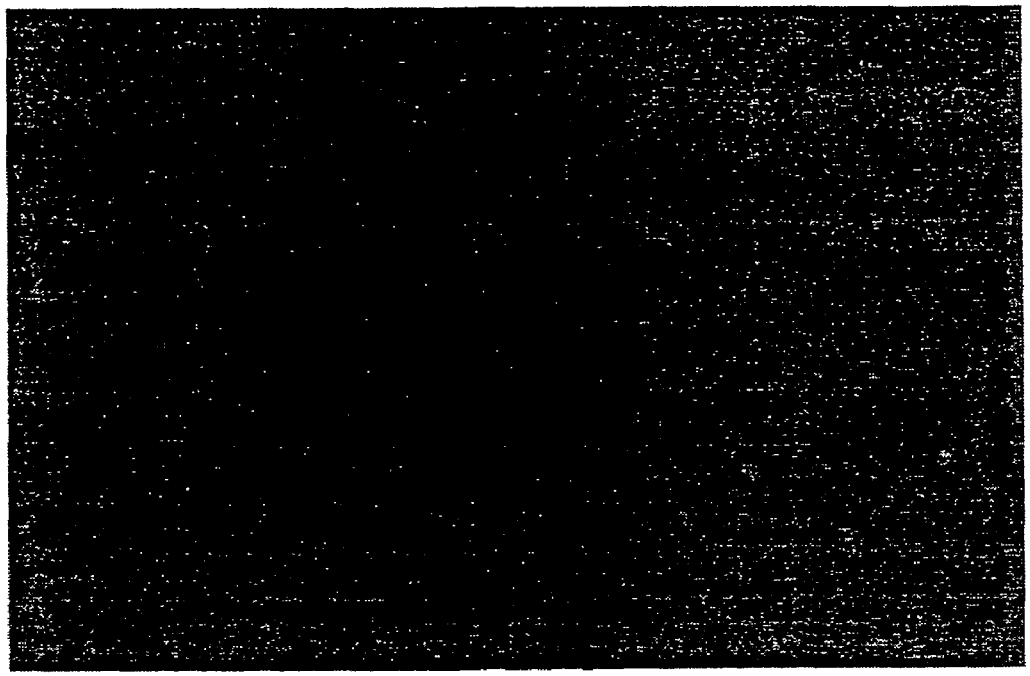
Figure 8C:
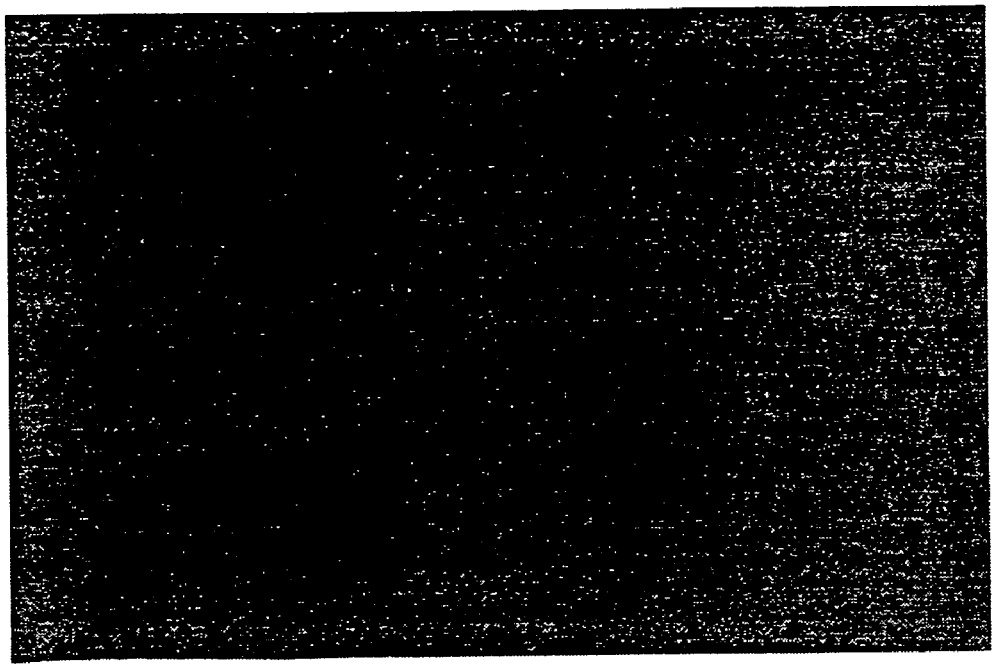
Figure 9:
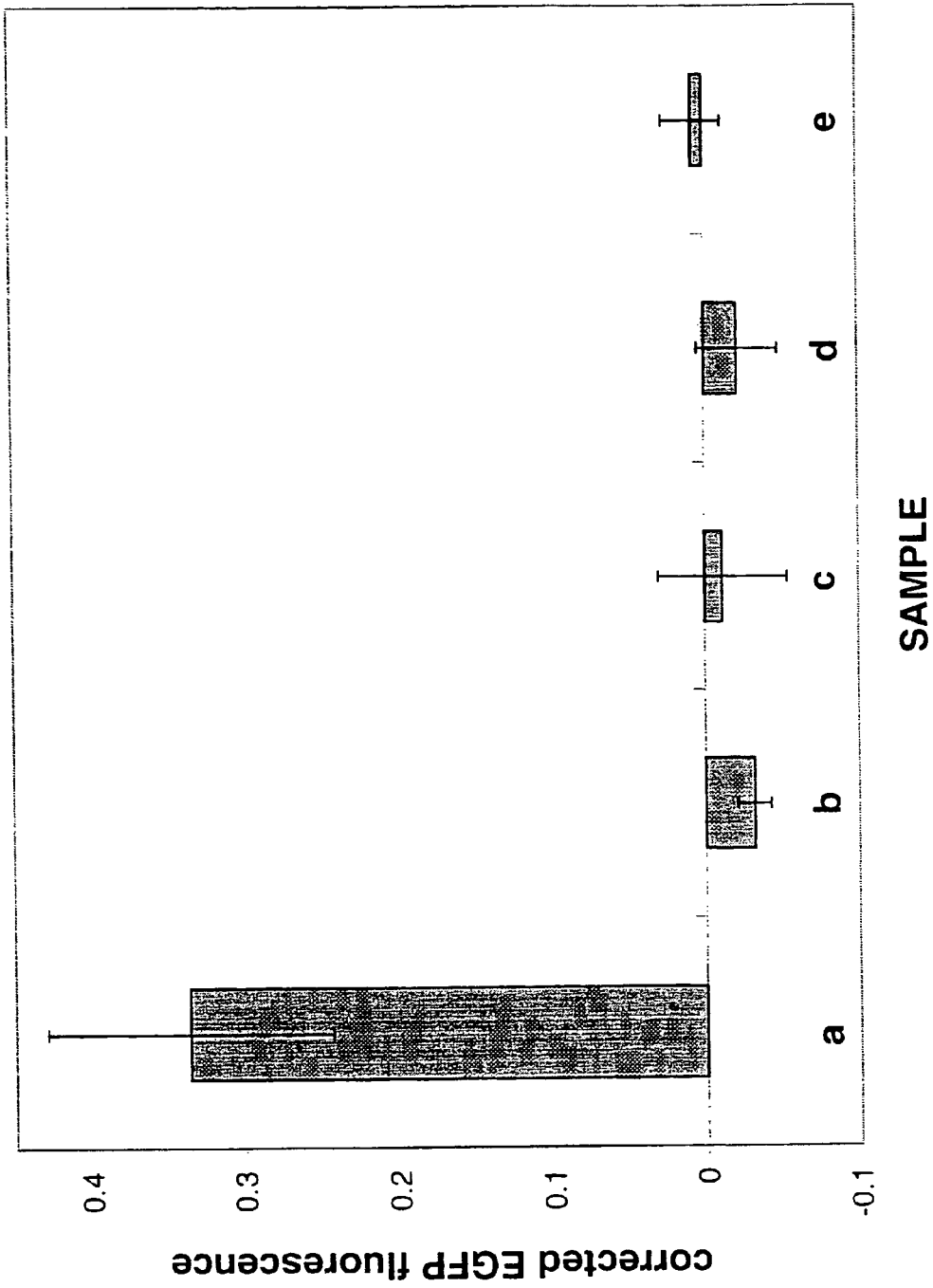
FIG. 9. Quantitation of EGFP expression in OVCAR 3 cells transfected with pEGFP-C1, as measured by the EGFP fluorescence level. Transfection experiments (a, b and c, see Example 11) were the same as in the previous figure legend. In addition, formulations tested were: d) egg PC liposomes prepared with spermine and pEGFP-C1 plasmid (see Example 3); and, e) no additions. The cells were washed and labeled with CBAM, and then dissolved in detergent to measure the fluorescence of EGFP and calcein blue (see Example 10; error bars are ±s.d).

Such successful expression was observed only where the transfected DNA had been polycation condensed; samples not processed with spermine exhibited none, or almost no, fluorescence (see FIG. 8). Quantification of fluorescent protein expression (FIG. 9) demonstrated that transfection with polycation-condensed DNA resulted in significant levels of expression, while transfection of samples processed without spermine did not result in quantifiable fluorescence. Moreover, transfection with free, i.e., unencapsulated, DNA also resulted in no observable or quantifiable fluorescence (FIGS. 8c and 9c).

This invention will be better understood from the following examples, which are merely exemplary of the invention as defined in the claims following thereafter.

EXAMPLES

Example 1

Materials

N-(lissamine rhodamine B sulfonyl)-phosphatidylethanolamine (transesterified from egg PC), DOPC, EPC and N-C12-DOPE were purchased from Avanti Polar Lipids (Alabaster, Ala.). OVCAR3 ovarian carcinoma cells were purchased from NCI-Frederick Cancer Research Laboratory (Frederick, Md.). The pEGFP-C1 plasmid, and E. coli DH5α competent cells were purchased from Clontech Laboratories (Palo Alto, Calif.). pZeoSVLacZ plasmid, competent cells and Hanahan's S.O.C. were purchased from Invitrogen (San Diego, Calif.). Hanks Balanced Salt Solution (HBSS), RPMI 1640 and heat inactivated fetal bovine serum and Lipofectin were purchased from Gibco/BRL (Grand Island, N.Y.). DNase-free RNase and RNase-free DNase I were purchased from Boehringer Mannheim (GmbH, Germany). Agarose was purchased from FMC Bioproducts (Rockland, Me.). Bacto agar, Bacto tryptone and yeast extract were purchased from DIFCO Laboratories (Detroit, Mich.). Calcein blue acetoxy methyl ester (CBAM), PicoGreen and SybrGreen I dyes were from Molecular Probes (Eugene, Oreg.).

Example 2

Plasmid Purification

Two plasmids were used in this study: the pZeoSVLacZ plasmid which is 6.5 kb, and expresses the lacZ gene for β-galactosidase in mammalian cells from the SV40 early enhancer-promoter, allowing selection in mammalian cells and E. coli using the antibiotic zeocin; and, the pEGFP-C1 plasmid, which is 4.7 kb and expresses enhanced green fluorescent protein (EGFP) from a human cytomegalovirus immediate early promoter, allowing selection in E. coli using kanamycin, and in mammalian cells using G418. Plasmids were purified from E. Coli (Baumann and Bloomfield, Biotechniques, 19: 884-890 (1995))—the final ratio of O.D. at 260 nm to O.D. at 280 nm was greater than 1.9 for all preparations; agarose gel electrophoresis indicated DNA in the expected size range.

Example 3

Liposomal-DNA Formulations

Samples were prepared by diluting 200 μg of DNA into 125 μl of LSB, and then combining the resulting suspension with 1 ml $CHCl_3$ containing 30 μmole of 70:30 molar ratio of N-C12 DOPE and DOPC, in a 13×100 Pyrex tube while vortexing. The sample was immediately sonicated for 12 seconds in a bath sonicator (Laboratory Supplies Co. Hicksville, N.Y.) under maximum power, to form an emulsion with plasmid DNA first. Subsequently, a 125 μl aliquot of LSB containing various concentrations of spermine (16 to 40 millimolar) was added to this emulsion with vortexing and sonication. Samples without spermine were prepared in the same way, except that spermine was omitted from the second 125 μl aliquot. Preparation of the samples with EPC was also identical, except that 7 mM spermine used.

Resulting emulsions were placed, within a few minutes, in a flask on a Rotovap (Büchi Laboratoriums-Technik AG, Switzerland). Organic solvent was removed while rotating the flask at its maximum rate, while the vacuum was modulated with a pin valve. Initially a vacuum of approximately 600-650 mm was established, this being subsequently increased, as rapidly as possible without excessive bubbling, until the maximum vacuum was reached (approximately 730 mm); the flask was then evacuated for another 25 minutes. The film left on the flask was resuspended in 1 ml of 300 mM sucrose in LSB, and the sample was extruded five times through 0.4 μm polycarbonate membrane filters (Poretics, Livermore, Calif.). The sample was then dialyzed against Hank's balanced salt buffer (HBSS) without $Ca^{2+}/Mg^{2+}$, overnight at 4° C.

Other lipid compositions were used to encapsulate condensed DNA according to the present invention. Plasmids were condensed and encapsulated into liposomes as described in this example above and sedimented as in Example 12. The lipid composition of the liposomes was cholesterol hemisuccinate: cholesterol: 1-palmitoyl-2-oleoyl-sn-glycero-3-phosphoethanolamine: 1,2-dioleoyl-sn-glycero-3-phosphoethanolamine: dioleoyl dimethylammonium propane:oleoyl acetate in a ratio of 12.5:2.5:50:12:10.5: 10.5. After pelleting and washing the DNA/lipid ratio for these liposomes was determined as in Example 10. Typical DNA/lipid ratios were 1.4-2.1 μg DNA per micromole of lipid.

Example 4

Spermine Partitioning

N-C12-DOPE bears a net negative charge which could potentially interact with positively charged spermine and affect the condensation process. Therefore, it was necessary to test the spermine partitioning between DNA and liposomes of this composition in a low salt buffer dialysis experiment. Experiments designed to measure the partitioning of spermine between negatively charged phospholipids and DNA were performed with a three chamber dialysis device (Sialomed, Md.)—each chamber contained 250 µl of liquid. The desired amount of spermine was diluted into LSB and placed in the center chamber, which was flanked by two 100,000 m.w. cutoff dialysis membranes. The chamber on one side of the spermine chamber contained 400 µg of pZeoLacZ plasmid DNA in a total volume of 250 µl LSB. The chamber on the other side contained either 250 µl of LSB alone, or empty N-C12 DOPE/DOPC (70:30) liposomes, prepared as described in Example 3 at a total lipid concentration of 30 mM, in 250l of LSB—in this arrangement, only spermine has access to all three chambers. Since it is known that neutralization of plasmid DNA by spermine leads to aggregation (FIG. 1), the turbidity of the solution in the DNA-containing chamber was used as a means of monitoring spermine partitioning. If the liposomes completely sequestered spermine away from the DNA, the DNA would not aggregate. The amount of available negatively charged lipid was approximately twice the amount of negative charge on the DNA in these experiments. Each dialysis device was rotated on a 12 inch motorized wheel overnight (approximately 20 hours). The DNA-containing chamber was then withdrawn with repeated pipetting to mix the sample, and it was placed in a 250 µl volume cuvette. The absorbance at 400 nm was used to monitor turbidity against the buffer background.

Figure 3:
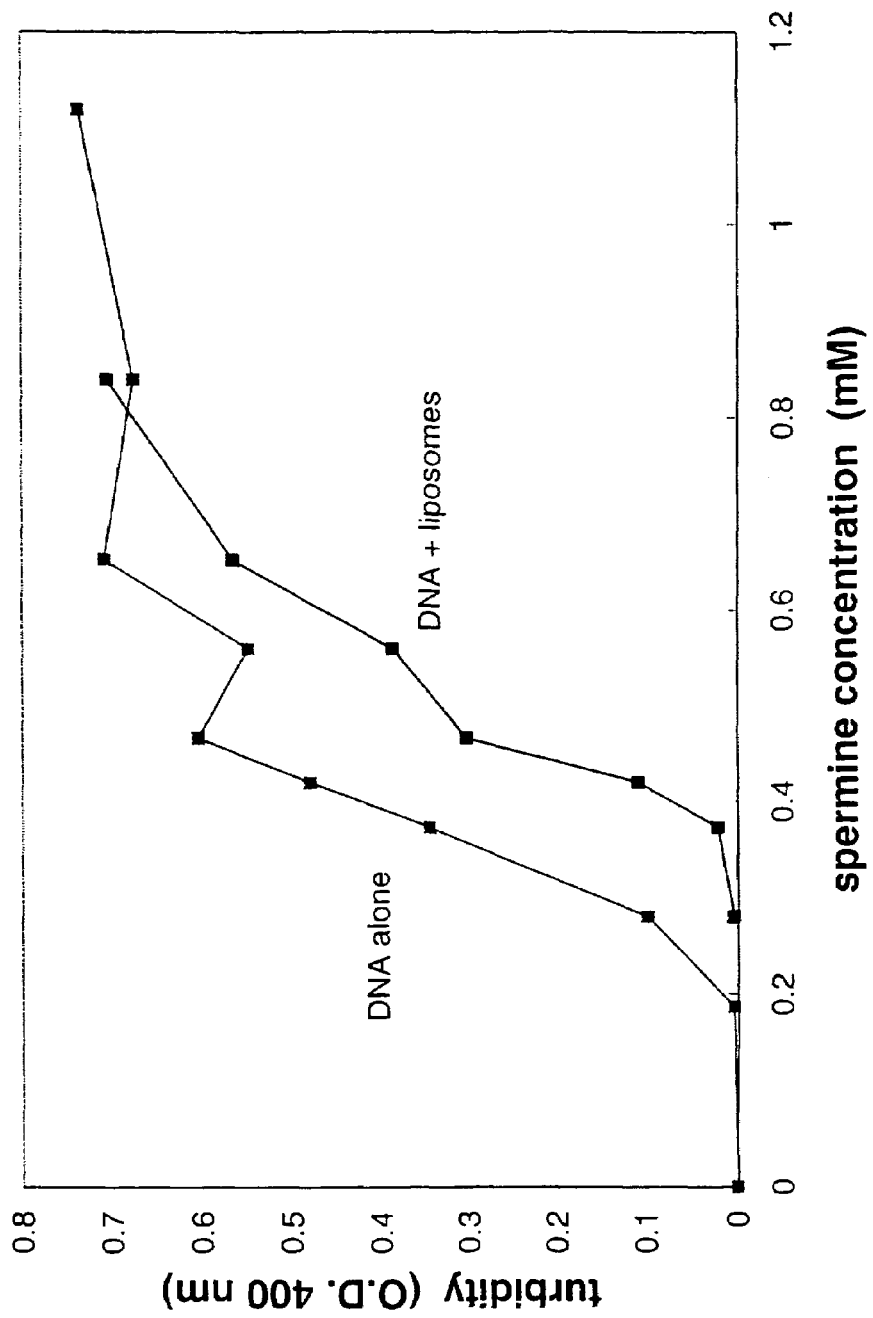
FIG. 3. Effect of liposomal N-C12 DOPE on spermine-mediated aggregation of plasmid DNA. Equilibrium dialysis was performed in a three-chamber dialysis device (see Example 4). The curve on the left is from dialyses without liposomes, while the curve shifted to the right is from dialyses that included a chamber with liposomes. X-axis: spermine concentration (mM); y-axis: turbidity (O.D. 400 nm).

Spermine titration curves of DNA turbidity were constructed for dialyses with, and without, liposomes present (FIG. 3). The approximate shift in the curve due to the presence of liposomes was used to calculate the relative binding constants for the lipids and the DNA, assuming that each spermine molecule binds to four nucleotide phosphate groups or four phospholipids, in simple equilibria with association constants $K_{DNA}$ and $K_{lipid}$, respectively. In low salt, the dissociation constant for spermine from DNA is know to be in the micromolar range (Wilson et al., Biochem, 18: 2192-2196 (1979); Gosule et al., J Mol Biol, 121: 327-337 (1978)). Therefore, the free concentration of spermine was taken as negligible at the millimolar spermine concentrations necessary for DNA aggregation in these experiments.

Fractional neutralization of the DNA phosphate groups by spermine required for DNA aggregation, γ, was taken as 0.9, based on the data obtained in the absence of liposomes. This is the same value reported to be required for DNA condensation, agreeing with the previous observation that aggregation accompanies condensation at high DNA concentrations (Wilson et al., Biochem, 18: 2192-2196 (1979); Gosule et al., J Mol Biol, 121: 327-337 (1978)). Assuming [DNA-spm]=γ [DNA]$_{total}$ at the point of aggregation and [lipid-spm]=the shift in the curve, one can use the equation $$K_{DNA}/K_{lipid}=[\gamma/(1-\gamma)]\times[(Lipid_{total}-shift)/(shift)]$$

When the Lipid$_{total}$ is taken as the total concentration of negatively charged lipid exposed on the outside of the liposomes divided by four, the ratio of apparent equilibrium constants is 178, i.e. the spermine binding to DNA is much more avid than binding to the lipids. The ratio of binding constants and the first factor on the right are constants. Therefore the last factor on the right can be used to calculate the shift in the spermine titration curve for DNA condensation for any total lipid concentration, including the higher effective concentration used in the emulsions.

The data presented in FIG. 3 demonstrates that the presence of the liposomes only slightly shifts the curve for DNA aggregation. Thus, approximately 0.6 mM spermine in the initial 250 µl emulsion was sufficient to condense the plasmid DNA, while a total of 0.85 mM would be sufficient to condense the DNA in the presence of the amount of N-C12-DOPE used. Therefore, it would be expected that the plasmid DNA can be truly condensed in these preparations without the complication of neutralization of the negatively charged lipids which could destabilize the liposomes.

Example 5

Light Microscopy of Liposome Samples

The precondensation of the DNA for potential encapsulation into liposomes was tested. Massive aggregation occurred as judged by a large turbidity change of the solution. This was not unexpected since similar problems have been reported. Light microscopy of plasmid aggregates (FIG. 1) was performed using 200 µg of pZeoLacZ plasmid in 125 µl LSB, mixed gently with 7 mM spermine in 125 µl LSB and incubated for 15 min at room temperature.

Figure 1B:
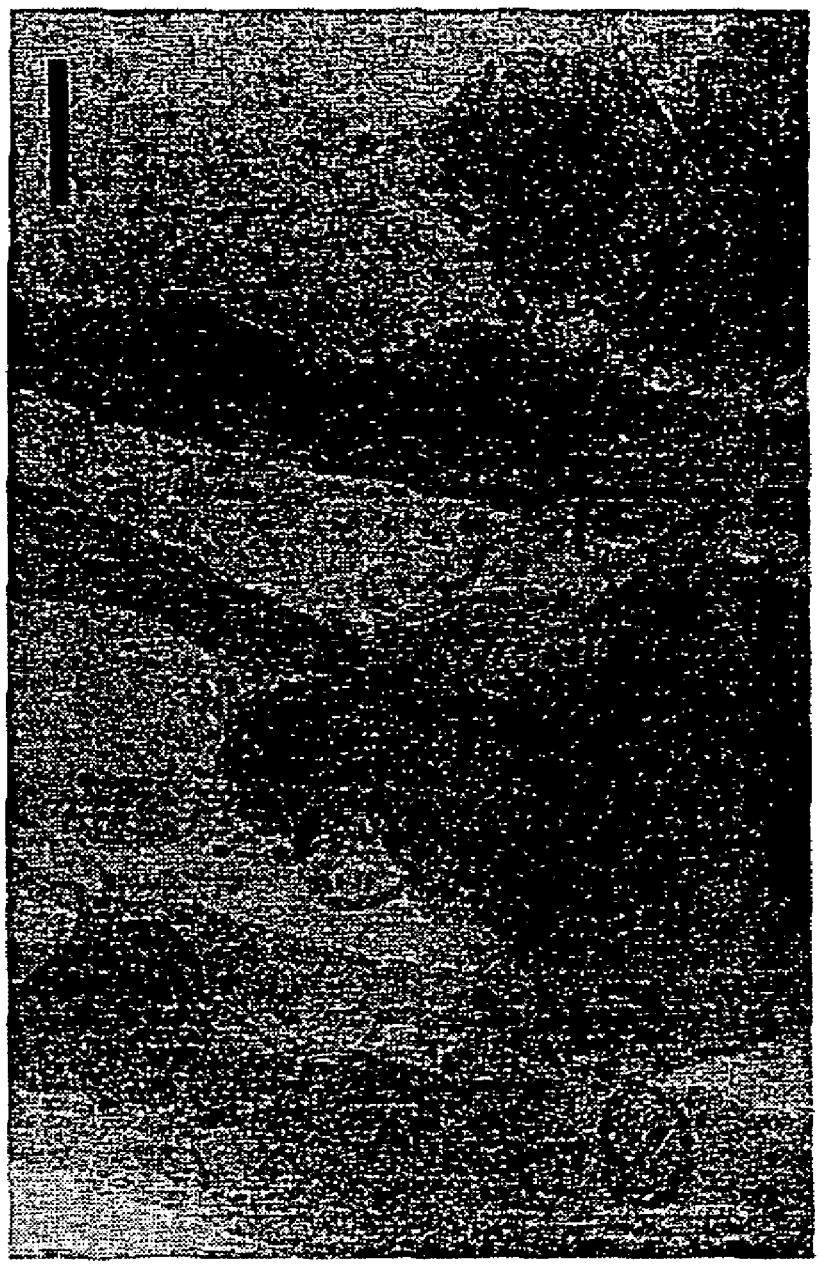

Microscopic observation (FIG. 1A) demonstrated that the aggregates were generally much larger than 1 µm and often as large as 5-10 µm. The large size of these aggregates was further confirmed by cryo-electron microscopy (FIG. 1B). Of particular note at this magnification are the regular arrays of fibers, perhaps as a result of spermine-induced condensation to a partially ordered structure. There were also some curved rods suggestive of the beginnings of toroidal structures, but no complete toroids. Aggregates formed in this way were too large to be useful for a delivery system.

For estimation of the size of N-C12-DOPE/DOPC (70:30) liposomes containing DNA (FIG. 5), polystyrene beads with an average diameter of 269±7 nm (Duke Scientific Corp., Palo Alto, Calif.) were diluted with H$_2$O to a concentration appropriate for microscopy, and samples of the N-C12-DOPE/DOPC (70:30)) liposomes containing DNA were used after extrusion and dialysis without further dilution (approximately 20 mM lipid). The samples were examined under an Olympus BH-2 fluorescence microscope (Olympus, Lake Success, N.Y.) at 1000×.

Figure 5A:
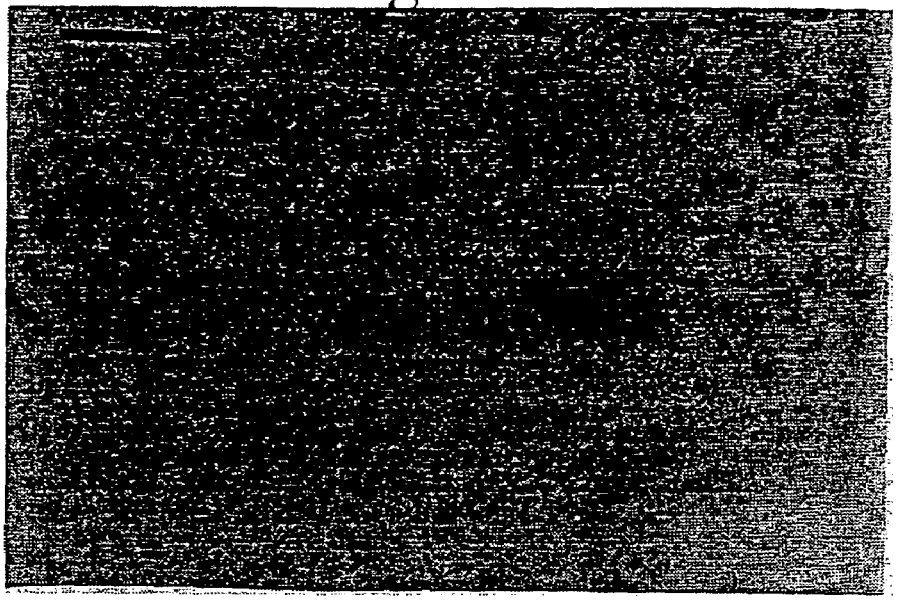
FIG. 5. Light micrographs of the particles in N-C12 DOPE/DOPC (70:30) sample prepared as described in Example 3 with pZeoLacZ plasmid and spermine (A) versus polystyrene beads with an average diameter of 269±7 nm (B) (bars represent 10 nm).
Figure 5B:

Results are presented in FIG. 5. The DNA-containing liposome particles appeared relatively uniform in size and shape at this magnification, and the approximate size of sample particles appeared very similar to those obtained from dynamic light scattering studies. Comparison of this DNA-containing liposome particles sample to the spermine-aggregated DNA in FIG. 1A demonstrates the benefit of condensing the DNA in the reverse micelles according to the present invention prior to forming the liposomes. There was no evidence of the very large aggregates observed when spermine interacted directly with DNA in aqueous solution, indicating that the emulsion condensation method may greatly inhibit such aggregate formation.

Example 6

Particle Analysis by Light Scattering

The N-C12DOPE/DOPC preparations were characterized by quasi-elastic light scattering. Particle size analysis was performed using a Nicomp 370 particle size analyzer (Particle Sizing Systems, Santa Barbara, Calif.). Samples were diluted approximately ten-fold for analysis. A Gaussian analysis was performed in the vesicle mode, and number weighted averages are reported. The data for spermine-condensed pZeoLacZ plasmid DNA prepared as in Example 3 could be fit by a Gaussian size distribution with a number average particle size of 222.6 nm.

Example 7

Freeze-Fracture TEM

The fusogenic N-C12DOPE/DOPC preparations with encapsulated DNA were further characterized by freeze fracture TEM. About 2 µl of sample was deposited between two Balzers copper double replicating holders and frozen in liquid propane. The sample was fractured at −100° C., $10^{-6}$-$10^{-7}$ barr and shadowed with platinum (<45° C.) and carbon in a Balzers BAF 400 freeze-fracture device. Replicas were digested with 5% bleach overnight, washed with distilled water and mounted on 300 mesh grids. The images were obtained with a Philips 300 TEM.

Figure 6:
FIG. 6. Freeze-fracture TEM micrographs (see Example 7) of N-C12 DOPE/DOPC (70:30) samples prepared with plasmid and spermine, as described in Example 3. Arrow points to the particle with apparently encapsulated material (bar represents 400 nm).

Results are presented in FIG. 6. Most of the particles were small in size (less than 400 nm), consistent with NICOMP results. Because of the prevalent fracture plane though lipid bilayers, observation of internal contents is rare with this technique. However, a small number of the particles appeared to have some encapsulated structures which could represent condensed DNA.

Example 8

Cryo Transmission Electron Microscopy

Cryo-EM was used to confirm the liposomal nature of the preparations and to possibly visualize any encapsulated materials. For EPC sample and spermine-aggregated DNA, copper grids coated with a holey carbon support were used without further treatment. For N-C12-DOPE/DOPC (70:30) DNA-containing liposome samples, EM grids with a holey carbon film were rendered positively charged by placing a drop of a 0.1 mM polylysine solution on the grid surface, and allowing it to sit for one min. The polylysine was blotted off and the grid rinsed with several drops of distilled water, followed by several drops of sample buffer. A 5 µl aliquot of sample was then placed on the grid, blotted to a thin film and immediately plunged into liquid ethane. The grids were stored under liquid nitrogen until used. They were viewed on a Philips CM12 transmission electron microscope (Mahwah, N.J.), operating at an accelerating voltage of 120 kV. A 626 cryoholder (Warrendale, Pa.) was used to maintain sample temperature between −177° C. to −175° C. during imaging. Electron micrographs were recorded of areas suspended over holes under low electron dose conditions. Magnifications of 35,000× or 60,000×, and underfocus values of 1.8-2.5 µm were used.

Figure 7A:
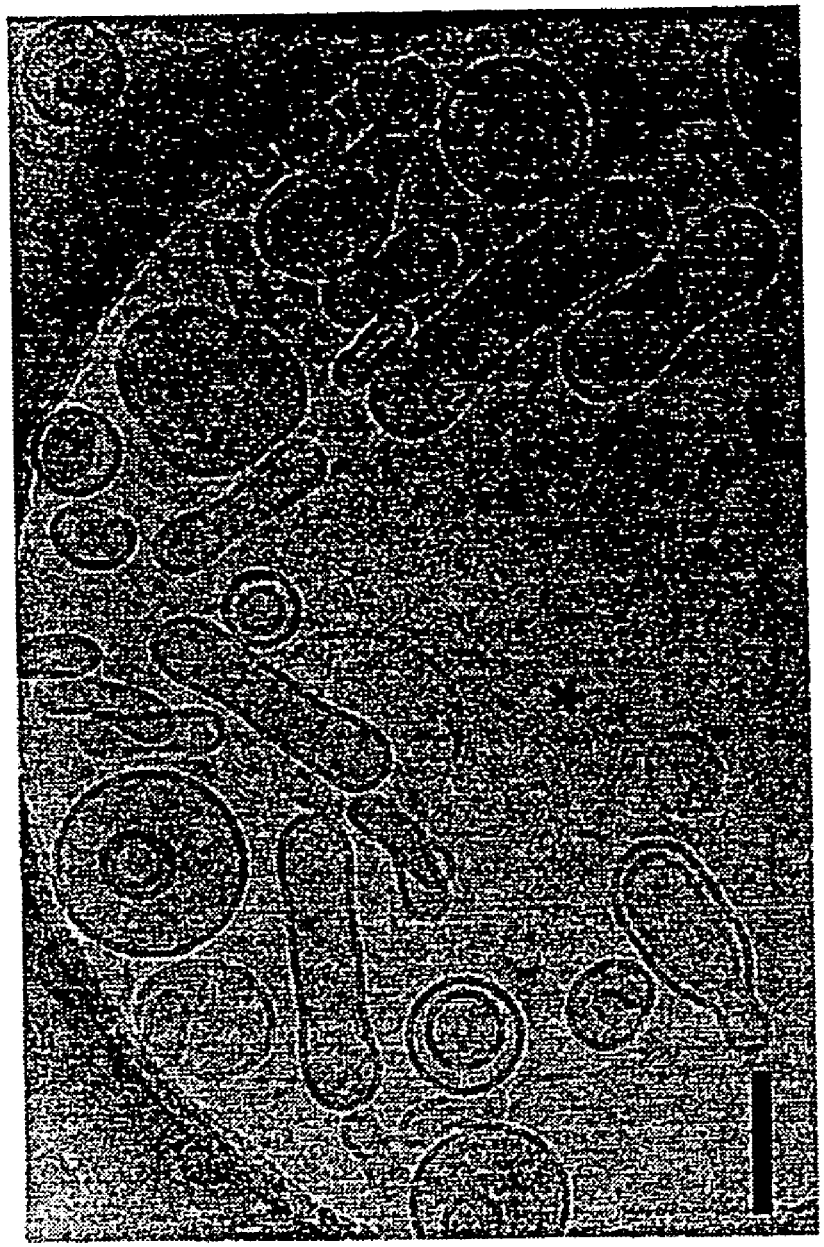
FIG. 7. Cryo TEM micrographs (see Example 8) of liposomes with N-C12 DOPE/DOPC and the pZeoLacZ plasmid without spermine (a), or with spermine (b), said liposomes being prepared as described in Example 3. In (a) fiber-like structures are seen outside (star) and apparently inside (arrow) liposomes. In (b), an arrow points to a toroid that resembles polycation condensed plasmid DNA (bars in (a) and (b) represent 100 nm). Photomicrograph (c) represents an EPC sample made with spermine. Toroid (arrow) and bent rod (star) structures are compared with multilamellar liposomes (pound sign) [bar represents 50 nm].

Results are presented in FIG. 7. When spermine was omitted from the procedure for the N-C12DOPE/DOPC liposomes, primarily unilamellar, relatively small but structurally heterogeneous liposomes were observed (FIG. 7a), consistent with the Nicomp analysis. A number of liposomes appeared tubular, probably as a result of the osmotic gradient generated during the preparation procedure. Some liposomes showed interior fiber-like structures possibly representative of uncondensed DNA (left arrow). Unencapsulated free fibers could also be seen (right arrow).

DNA containing N-C12DOPE/DOPC liposome samples prepared with spermine (FIGS. 7b,c) were also heterogeneous in size, shape and lamellarity. Some particles were normal-looking liposomes with no visible encapsulated material. However, others contained electronically dense, well defined toroidal structures (FIG. 7b, arrows) that were not seen in the samples without spermine. Such structures were not related to the particular lipid used, as toroidal (FIG. 7c, right arrow) and bent rod structures (FIG. 7c, left arrow) were also observed in egg PC preparations, which tended to be more stable under the cryo-EM sample preparation conditions. The spacing between the fine lines within the rods and toroids were uniform and significantly smaller than the spacing between two membranes in multilamellar liposomes (star). These toroidal structures bear great resemblance to the toroids and rods observed when free DNA is condensed by spermine (Chattoraj et al., *J Mol Biol,* 121: 327-337 (1978)) or other condensing agents (Arscott et al., *Biopolymers,* 30: 619-630 (1990); Gosule and Schellman, *J Mol Biol,* 121: 327-337 (1978)) in dilute solutions. The parallel and concentric fine lines visible within the rods and toroids also resembled the lines seen within the plasmid aggregates (FIG. 1b).

Figure 7B:
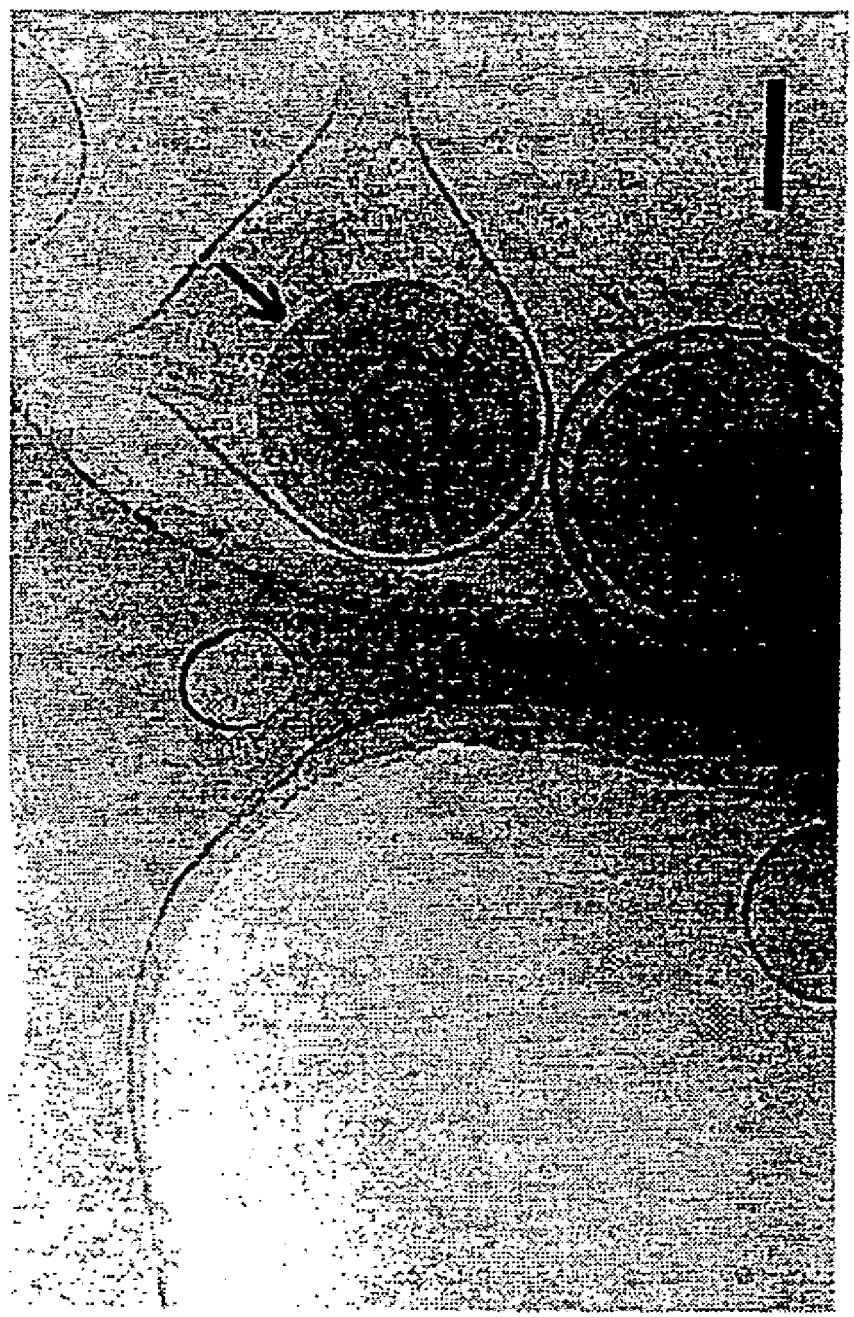
Figure 7C:
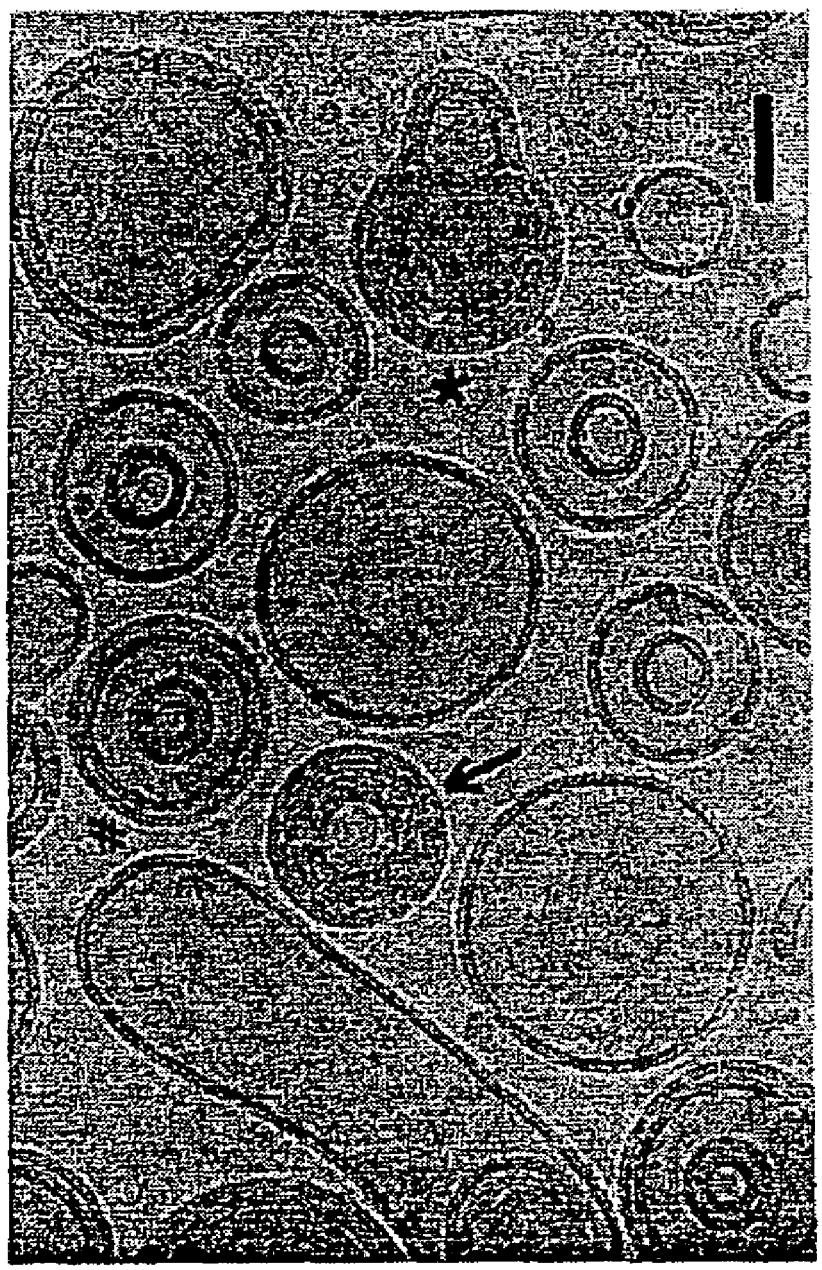

Membranes could be clearly observed around some of the toroidal structures (e.g. FIG. 7b). It is likely that all of the observed toroids are encapsulated within an ion-impermeable barrier, since condensed DNA toroids cannot exist in the high salt buffer in which the liposomes were ultimately suspended. Therefore, it would appear that a major portion of these preparations consists of liposomally encapsulated plasmid DNA.

Example 9

Agarose Gel Analysis

Protection of plasmid DNA from DNase digestion was evaluated by agarose gel electrophoresis for liposomally encapsulated plasmid DNA prepared with spermine and a control sample prepared without spermine. A 50-µl aliquot of the desired preparation was diluted into 145 µl HBSS without Ca2+/Mg2+, and 1 µl of 0.2 M MgCl2 plus 2 µl DNase 1 (20 units) were added with mixing. After a 6 hr incubation at room temperature, 2 µl of 0.5 M EDTA was added to stop the reaction. For undigested controls, a 50 µl aliquot of each sample was mixed with 150 µl HBSS (w/o Ca2+/Mg2+). Samples were then extracted with phenol/$CHCl_3$/isoamyl alcohol and precipitated with ethanol as described (Sambrook et al., *Molecular cloning: A laboratory manual,* 2nd ed. Cold Spring Harbor Laboratory Cold Spring Harbor, N.Y., pp B4-B5 (1989)). The pellet was dissolved in 20 µl TE (pH 8.0), 5 µl of which was loaded on a 0.8% agarose gel. The gels were stained with a 1:10,000 dilution of stock SYBR Green I nucleic acid gel stain (Molecular Probes) for 30 minutes, and visualized on a FotoSpectrum® ultraviolet transilluminator (light box). Photographs were taken on the light box with a Polaroid MP 4+ camera system. These photographs were then scanned on a ScanJet IIC® (Hewlett Packard, Palo Alto, Calif.) and digitized with Aldus Photostyler® (U-Lead Systems, Torrance, Calif.).

Figure 4:
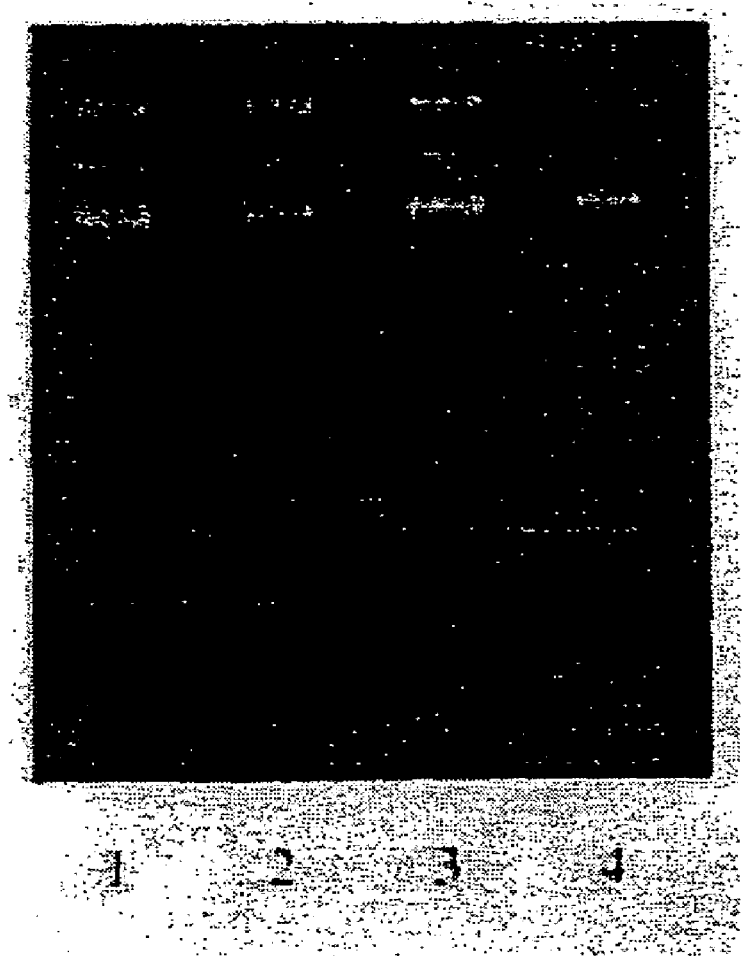
FIG. 4. Agarose gel analysis of plasmid DNA protection in N-C12 DOPE/DOPC (70:30) formulations—an aliquot from each preparation after is extrusion and dialysis was divided, and one part digested with DNase I (see Example 9). Lane 1. Preparation without spermine. Lane 2. Same as lane 1 but digested with DNase I. Lane 3. Preparation with spermine. Lane 4. Same as lane 3, but digested with DNase I.

Results are presented in FIG. 4 demonstrate that both preparations allowed significant DNA protection or apparent encapsulation.

Example 10

Quantitation Analysis

To quantitate DNA protection, DNA was extracted from each aliquot and measured by a fluorescent assay. PicoGreen fluorescent assays (Haugland, *Handbook of fluorescent probes and research chemicals,* 6th ed. Molecular Probes, Inc., pp 161-162 (1996)) were used to quantitate DNA that had been extracted by the phenol/chloroform procedure set forth in Example 9. A working solution was prepared by adding 100 µl PicoGreen stock (Molecular Probes) to 20 ml TE (pH 7.5). The extracted sample was first diluted 100× with TE (pH 7.5). Then a 14 µl aliquot of the diluted sample was mixed with 986 µl TE (pH 7.5) and 1 ml PicoGreen working solution. The mixture was incubated in the dark at room temperature for 4 minutes. The PicoGreen fluorescence was recorded at room temperature on a PTI Alphascan fluorometer (South Brunswick, N.J.), with excitation wavelength of 480 nm, and emission wavelength of 520 nm, with a >500 nm highpass filter (Schott Glass Technologies, Duryea, Pa.). The fluorescence of 1 ml TE (pH 7.5) and 1 ml PicoGreen working solution mixture was used as blank. The percent DNA being protected from DNase I digestion was calculated by subtracting the blank, and taking the undigested sample as 100%. Under our experimental conditions, the fluorescent signal from digested DNA was insignificant.

The sample with spermine displayed 10.1±5.6 percent plasmid protection, while 19.0±4.5 was protected in the sample without spermine.

Example 11

Transfection Assays

The transfection activity of the liposomal preparations encapsulating pEGFP-C1 plasmid DNA was then tested. OVCAR3 cells were plated at $1 \times 10^5$ cells per ml in 24-well plates, or at $2 \times 10^5$ cells per ml in 96-well plates in 1 ml or 0.1 ml per well, respectively, of RPMI 1640 with 10% heat inactivated fetal bovine serum. Cells were allowed to grow for two days (approximately 40-48 hours) before transfections were performed; at this point the cells were at confluency. Transfection solutions were prepared by dilution of appropriate liposome or DNA samples into serum-free medium. The plates were aspirated to remove medium and washed once with Dulbecco's phosphate buffered saline followed by aspiration.

Transfection solutions (0.5 ml per well for 24-well plates, 0.1 ml per well for 96-well plates) were prepared by dilution of dialyzed samples containing the pEGFP-C1 plasmid 10-fold into serum-free medium (approximately 2 mM total lipid unless indicated otherwise), and were then added to the wells and incubated at 37 degrees C. for 3 hours. The wells were aspirated, and medium containing 10% heat inactivated fetal bovine serum was added to each well. Because of the previously demonstrated silencing of transgenes under the CMV promoter (Tang et al., *Human Gene Therapy,* 8: 2117-2124 (1997); Dion et al., *Virology,* 231: 201-209 (1997))5 µM of the histone deacetylase inhibitor, trichostatin A, was added to each well to enhance expression. In the experiments presented in the last 2 figures, another histone deacetylase inhibitor, 5 mM sodium butyrate, was used instead.

After incubation at 37 degrees C. in a cell culture incubator for 18-22 hours, the medium was aspirated and washed with 0.5 ml aliquots of Dulbecco's PBS. Photomicrographs were taken of the samples still on tissue culture plates with an Olympus IMT-2 inverted microscope using the 10× objective. The PBS was aspirated and 0.5 ml (0.1 ml for 96 well plates) of 5 µM calcein blue acetoxy methyl ester (CBAM) in PBS was added to each well and incubated for 40 minutes at room temperature. Cells were washed again with PBS, aspirated, and 0.5 ml (0.1 ml for 96 well plates) of 1% $C_{12} E_8$ in TE buffer (pH 8.0) was added to each well. The samples were then dissolved in detergent and readings were taken for corrected total EGFP fluorescence, in terms of the total number of live cells. Fluorescence of the plates was measured in a Cytofluor II fluorescent plate reader (PerSeptive Biosystems, Framingham, Mass.). Readings for calcein blue loaded in live cells were made at excitation 360 nm and emission of 460 nm with a gain of 80. These readings were verified to be linear with the number of cells originally plated up to a level where confluence was observed. For the data shown in FIG. 10, a liposomal pellet separated from external DNA was used (Example 12). Because the $Ca^{2+}$ and $Mg^{2+}$ levels in RPMI 1640 are significantly lower than in serum, the data in FIGS. 11 and 12 were obtained after supplementing the serum-free medium with $Ca^{2+}$ and $Mg^{2+}$ to attain 1.2 and 0.8 mM, respectively, during the transfection.

An approximate conversion to EGFP fluorescence per unit cellular protein could be estimated by measuring the average protein concentrations of 48 hour cultures of the OVCAR-3 cells in 24 and 96 well experiments extracted with 1% Triton-100 detergent. A bicinchoninic acid assay (Pierce Chemical, Rockford, Ill.) was used with bovine serum albumin as a standard. For FIG. 9, bar "a," the total average background-corrected fluorescence reading per well was 670 units. From a separate plate, the average total cellular protein per well at the time of transfection (48 hr.) was approximately 88.4 µg/well giving 7.6 fluorescence units per µg of total cellular protein in a volume of 0.5 ml for the 24 well plate experiments. In FIG. 10, the data for bar "a" (96 well experiment), represents an average background-corrected EGFP fluorescence of approximately 420 units per well with an average total cellular protein concentration of 27 µg per well, giving 15.5 fluorescence units per µg of total cellular protein in a total volume of 0.1 ml. In FIG. 11, (96 well experiment), the bar "a" fluorescence reading was 103 fluorescence units per µg of cellular protein.

To model intraperitoneal delivery (data in FIGS. 11 and 12), the transfection was performed by first adding 50 µl of a concentrated cell-free lavage fluid from the peritoneal cavity of tumor-bearing SCID mice (Example 13) to each aspirated well of a 96-well plate with OVCAR-3 cells grown as described above. To each well was added 50 µl of an N-C12-DOPE/DOPC liposome-DNA formulation, prepared as described in Example 3, and resulting in a final lipid concentration of approximately 10 mM and a final encapsulated DNA concentration of approximately 7-14 µg/ml (total DNA of 67 µg/ml). Incubations were performed as described above. In this case, the peritoneal lavage fluid was adjusted to approximately serum levels of $Ca^{2+}$ and $Mg^{2+}$ (1.2 mM and 0.8 mM, respectively) by adding a concentrated stock. The liposomal-DNA solution was also adjusted to the same levels of $Ca^{2+}$ and $Mg^{2+}$ by addition of the concentrated stock just before addition of the liposomes to the cells.

Figure 12A:
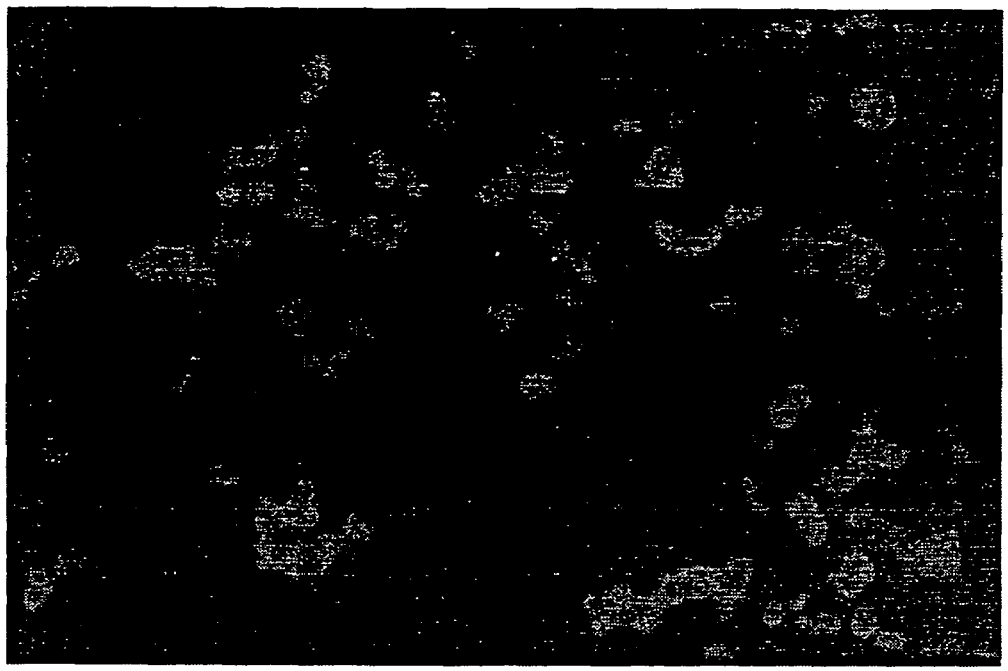
FIG. 12. Fluorescent photomicrographs of OVCAR-3 cells transfected (see Example 11) with to N-C12 DOPE/DOPC (70:30) liposomes in buffer or mouse ascites fluid. Cells treated as described in the legend to FIG. 12 were photographed. Photograph A represents transfection without peritoneal ascites fluid and photograph B with peritoneal ascites fluid; cells are confluent in these views.
Figure 12B:
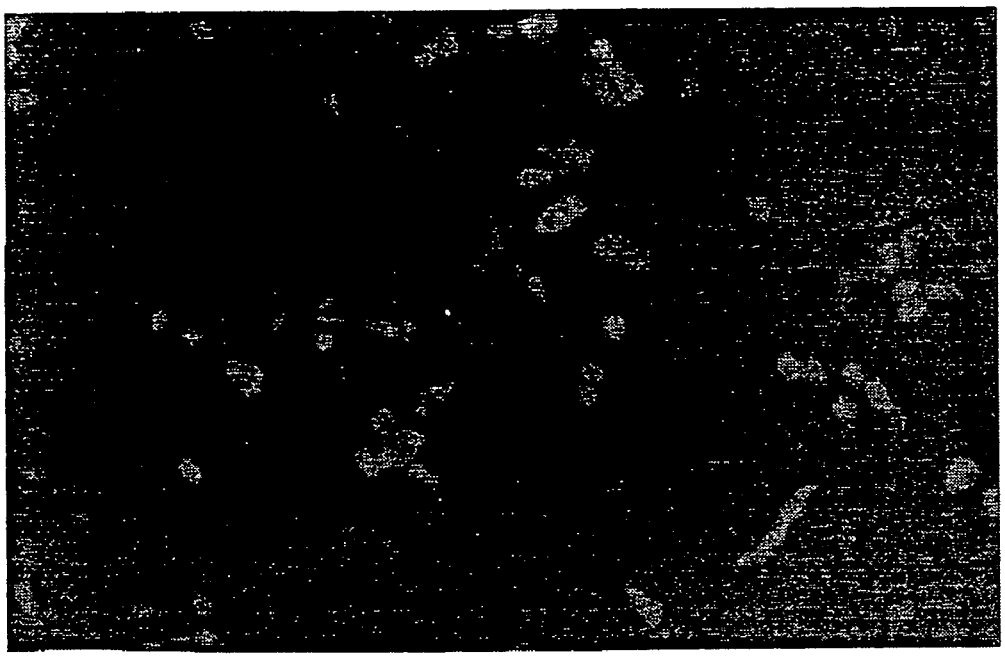

The data in FIGS. 8 and 9 demonstrate that the formulation of NC12-DOPE/DOPC (70/30) liposomes encapsulating spermine-condensed plasmid DNA was active in transfection of OVCAR-3 cells. The data show that the activity was dependent on the presence of the spermine condensing agent and on the encapsulation of the plasmid DNA within the liposomes. The data in FIG. 10 demonstrate again that the transfection activity is associated with lipid-encapsulated DNA and not free external DNA. The data in FIGS. 11 and 12 show that transfection can also occur in the presence of the potential interfering substances (e.g. serum proteins) found at the intraperitoneal site of the OVCAR-3 tumors.

Example 12

Sedimentation of Plasmid DNA and Lipid Particles

In order to demonstrate the transfection activity of the encapsulated plasmid DNA, it was necessary to separate free plasmid DNA from liposome-encapsulated DNA. The following preparation method was utilized. Liposomes, prepared by sedimentation to removed external DNA, were used in the experiments, the results of which are shown in FIG. 10. For sedimentation experiments, N-C12-DOPE/DOPC (70:30) liposome samples were prepared by the method of Example 3 with spermine, except that 200 mM sucrose was included in the LSB. Headgroup labeled lissamine rhodamine B-phosphatidylethanolamine (Rh—PE) was also added as a lipid probe at 10 μg/ml. A 500 μl aliquot of the preparation was then centrifuged at 16,000×g for 3 hours. After the supernatant was removed, the pellet was resuspended in HBSS without $Ca^{2+}/Mg^{2+}$. The suspension was centrifuged at 16,000×g for 3 hours. The pellet was resuspended in 500 μl HBSS without $Ca^{2+}/Mg^{2+}$. Aliquots of 50 μl of each fraction were taken for DNase I digestion (Example 9). After phenol/$CHCl_3$ extraction and ethanol precipitation, the plasmid DNA in each aliquot was measured by PicoGreen assay (Example 10) and used to calculate the percentage of protected plasmid, and the percentage of total plasmid DNA, in each fraction.

For measurement of the distribution of lipids, a 40-μl aliquot of each fraction was dissolved in 0.2% $C_{12}E_8$ in a total volume of 2 ml and the fluorescence monitored with an excitation wavelength of 560 nm with a 550±20 nm bandpass filter (Melles Griot, Irvine, Calif.), and an emission wavelength of 590 nm. As a control, empty N-C12-DOPE/DOPC (70:30) liposomes were prepared as above. After dialysis, 100 μg of EGFP plasmid was added to 500 μl of the sample. The sample was then centrifuged and quantitated for lipids and plasmid DNA.

Approximately 80% of the lipid pelleted under these conditions, while only about 14% of the total DNA pelleted. The transfection activity of the pelleted material is shown in FIG. 10. Transfection activity was clearly associated with the lipid pellet, i.e., with the liposome encapsulated DNA.

Example 13

Lavage Fluid

In order to test the effect of the intraperitoneal proteins on the transfection activity of the preparations described herein, a lavage fluid was prepared as described below. A cell-free 6 ml HBSS lavage was taken from a SCID mouse 7 weeks after injection of OVCAR-3 cells and was concentrated to 1 ml with a 10,000 mw cutoff spin concentrator. Protein recovery is approximately 60%. This fluid comprising approximately 10 mg/ml protein in HBSS was supplemented with $Ca^{2+}$ and $Mg^{2+}$ to within the normal serum range, added to cultured OVCAR-3 cells and gently mixed in equal volume with liposomes in HBSS at the same Ca/Mg level, to give a final lipid concentration of 10 mM.

The results of these transfection experiments are shown in FIGS. 11 and 12. Despite the known inhibitory effects of serum proteins on transfection efficiency, substantial activity remained under these conditions using the formulation prepared by the method of the present invention.

Example 14

Liposome Loading Efficiency

The efficiency of the loading of liposomes using a precondensed DNA method was compared to the method described herein. Liposomes were prepared as described by Ibanez et al., *Biochem Cell Biol*, 74: 633-643 (1996). pEGFP plasmid DNA was dissolved at 66 μg/ml in TS buffer (10 mM Tris, 1 mM NaCl, pH 7.0). 2 ml of this solution was mixed with 2 ml of 23 mM spermidine in TS buffer to precondense the DNA yielding a very cloudy solution. This was stored overnight at 4° C. The next day, a total of 9 μmol of lipid was dissolved in 1 ml of diethyl ether. To this was added 330 μl of the DNA and spermidine solution with vortexing. The mixture was then immediately sonicated three times for 5 seconds each (Laboratory Supply sonicator #G112SOI). The diethyl ether was then removed using a rotary evaporator at 37° C. to form liposomes. Four such samples were prepared for each lipid composition. The liposomes were pelleted at 200,000×g for 30 minutes. The supernatant was removed and 500 μl more TS buffer added and the centrifugation repeated. After three total cycles, the liposomes were extruded through MF membranes with 0.45 μm pores. Liposomes were used for determination of encapsulation at this point or a portion of them were dialyzed against Hanks balanced salt solution without $Ca^{2+}$ or $Mg^{2+}$. For comparison liposomes were also prepared as described in example 3. DNA encapsulation was measured as described in examples 9 and 10. All digestions were for 6 hours. Lipid concentration was measured by HPLC. All components but cholesterol were quantitated using a Waters Sherisorb silica column (3 μm) with a mobile phase of acetonitrile:methanol:$H_2SO_4$, 100:3:0.05, and detected by UV absorbance. Cholesterol was measured on a Phenomenex Luna C18 column (5 μm) with a mobile phase of 96:4 methanol:water and detected by an elastic light scattering detector. Lipid compositions tested are given in the table below.

TABLE 1

| | DNA/lipid ratio: (μg DNA/μmol total lipid)* | |
| --- | --- | --- |
| Formulation | Pre-digestion | post digestion |
| Literature values:** | | |
| EPC:CHOL (1:1) | 1.00 | |
| EPC:Brain PS:CHOL (4:1:5) | 2.87 | |
| EPC:EPA:CHOL (4:1:5) | 2.64 | |
| EPC:cardiolipin:CHOL (5:1:4) | 2.53 | |
| Low salt (10 mM Tris): | | |
| EPC:CHOL (1:1) | 0.52 | 0.07 |
| EPC:Brain PS:CHOL (4:1:5) | 0.70 | 0.01 |
| EPC:EPA:CHOL (4:1:5) | 0.48 | 0.04 |
| EPC:cardiolipin:CHOL (5:1:4) | 0.78 | 0.09 |
| Isotonic salt after preparation: | | |
| EPC:CHOL (1:1) | 0.42 | 0.10 |
| EPC:Brain PS:CHOL (4:1:5) | 0.78 | 0.08 |
| EPC:EPA:CHOL (4:1:5) | 1.63 | 0.16 |

TABLE 1-continued

DNA/lipid ratio: (μg DNA/μmol total lipid)*

| Formulation | Pre-digestion | post digestion |
|---|---|---|
| EPC:cardiolipin:CHOL (5:1:4) | 0.65 | 0.20 |
| TLC 70:30 formulation | 8.53 | 0.59 |

*Lipid recovery estimated by HPLC. DNA quantitated by extraction and PicoGreen assay.
**Ibanez, M., Gariglio, P., Chavez, P., Santiago, C. W. and Baeza, I. (1996) "Spermidine-condensed DNA and cone shaped lipids improve delivery and expression of exogenous DNA transfer by liposomes," Biochem Cell Biol, 74: 633-643 (1996).

Liposomes prepared by condensation of DNA within an emulsion as described herein resulted in much higher DNA:lipid ratios than liposomes prepared with precondensated DNA.

Example 15

Determination of Lamellarity of Liposomes

Figure 13:
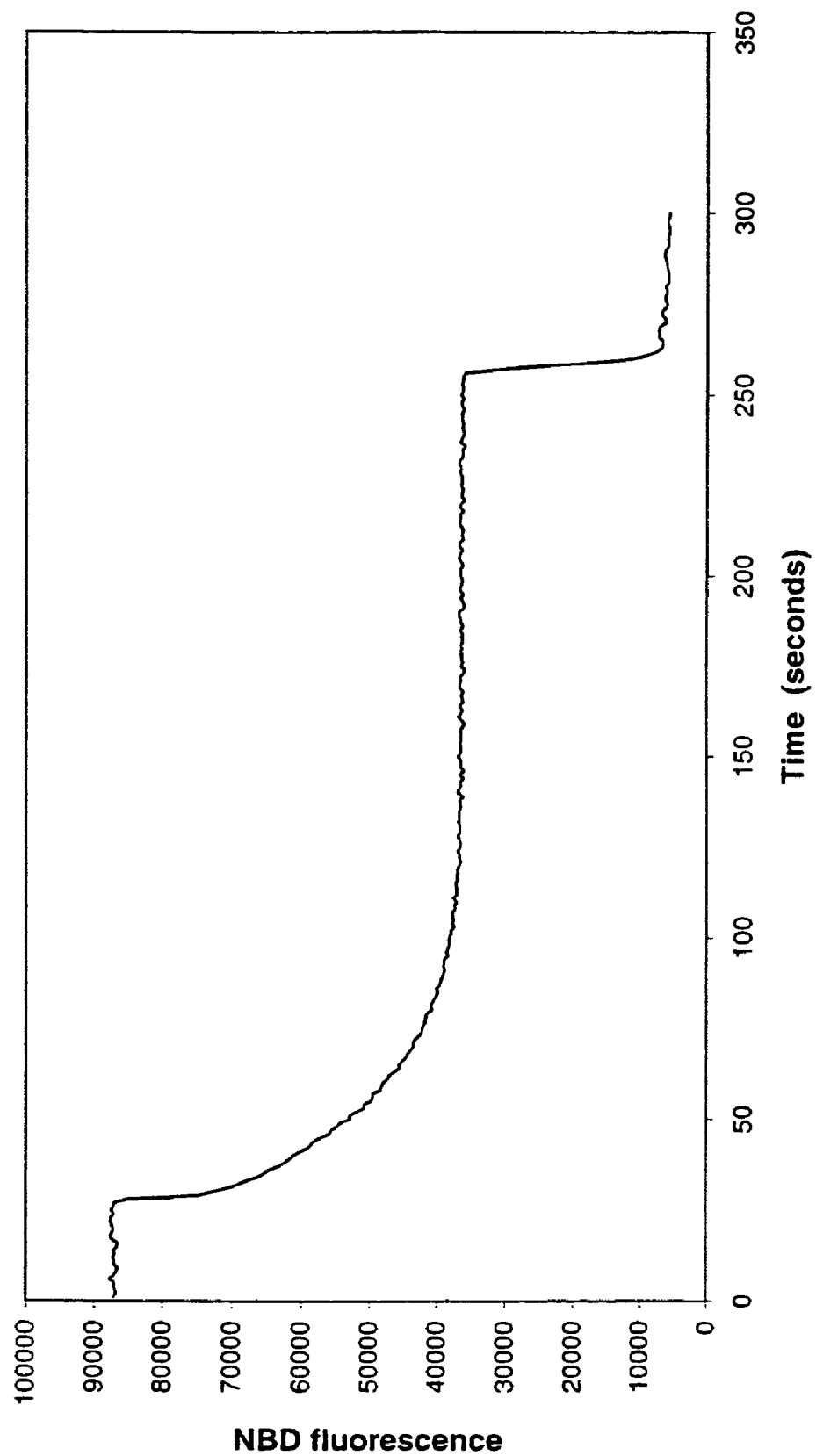
FIG. 13. Fluorescent probe determination of liposome lamellarity.

Liposomes composed of 70:30 N-C12-DOPE/DOPC and encapsulating plasmid DNA were prepared as described in Example 3 and sedimented and washed as in Example 12. These liposomes also contained an NBD probe at 0.5 mole % of the total lipid. Liposomes were diluted to 80 μM total lipid concentration in phosphate buffered saline in a stirred fluorometer cuvette. NBD fluorescence was measured with excitation at 450 nm and emission at 530 nm. A final concentration of 20 mM sodium dithionite was injected into the cuvette with the liposomes to reduce exposed NBD probe. FIG. 13 demonstrates that approximately 50-55% of the NBD signal disappeared indicating that the liposomes in the preparation were primarily unilamellar, i.e. about half the lipid probes were exposed to the membrane-impermeable reducing agent, sodium dithionite.

Example 16

Transfection of Subcutaneous Human Tumor in SCID Mice by Intratumoral Injection

Human OVCAR-3 cells (2×10$^6$) were injected subcutaneously into SCID mice and allowed to grow for several weeks until an average diameter of approximately 4-7 mm was reached.

Liposomes containing spermine, the pEGFP-C1 plasmid and 70 mole % of N-C12-DOPE and 30 mole % of DOPC were prepared as in Example 3. The liposomal membranes also contained 0.5 mole % Rhodamine-PE as a fluorescent liposome marker.

0.11 ml of a liposome solution in Hanks Balanced Salt Solution without calcium or magnesium (HBSS) at a total lipid concentration of approximately 40 mM was injected directly into the center of the tumors after adjustment of $Ca^{2+}$ and $Mg^{2+}$ levels to 1.2 and 0.8 mM, respectively. One day later, 0.11 ml of 20 mM sodium butyrate in HBSS was injected at the same sites. After 24 hours, tumors were excised and frozen. Later, 14-30 μm thick sections were obtained on a cryostat instrument at −20° C. and mounted frozen onto glass cover slides and secured with a cover slip. Frozen tumor samples were mounted in O.C.T. embedding medium.

Figure 14A:
FIG. 14. Fluorescent photomicrographs of OVCAR-3 tumor transfected in vivo with N-C12 DOPE/DOPC (70:30) liposomes containing pEGFP-C1. Panel A depicts the expression of EGFP. Panel B depicts the red fluorescence from rhodamine—labeled liposomes.
Figure 14B:
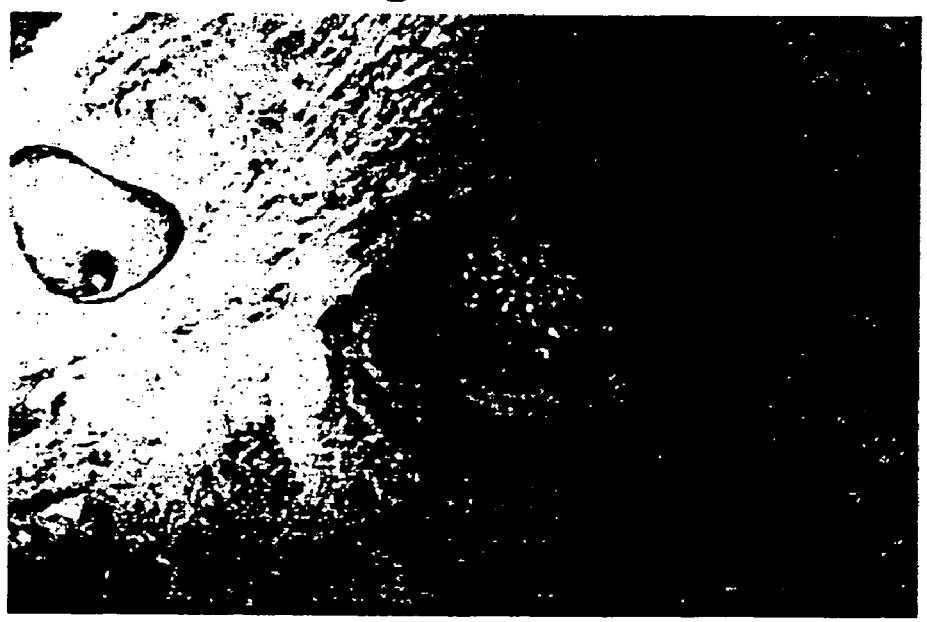
Figure 15A:
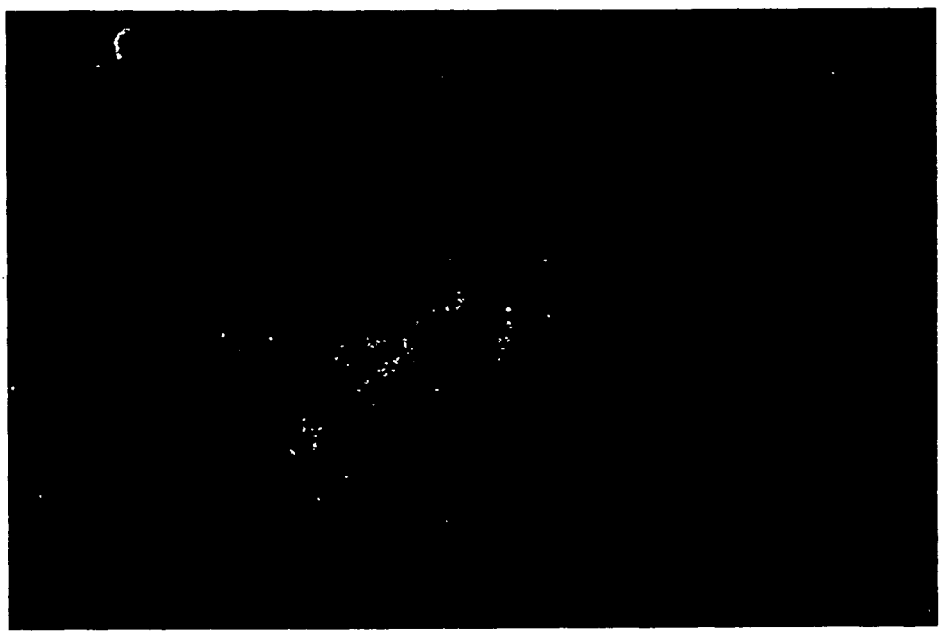
FIG. 15. Fluorescent photomicrographs of OVCAR-3 tumor taken from a different site than FIG. 14 transfected in vivo with N-C12 DOPE/DOPC (70:30) liposomes containing pEGFP-C1. Panel A depicts the expression of EGFP. Panel B depicts the red fluorescence from rhodamine—labeled liposomes.
Figure 15B:
Figure 16A:
FIG. 16. Fluorescent photomicrographs of control tumor tissue. Panel A depicts diffuse green fluorescence. Panel B depicts the lack of red fluorescence from rhodamine—labeled liposomes FIG. 17. Graph depicting expression of β-galactosidase activity in muscle tissue after transfection in vivo.
Figure 16B:
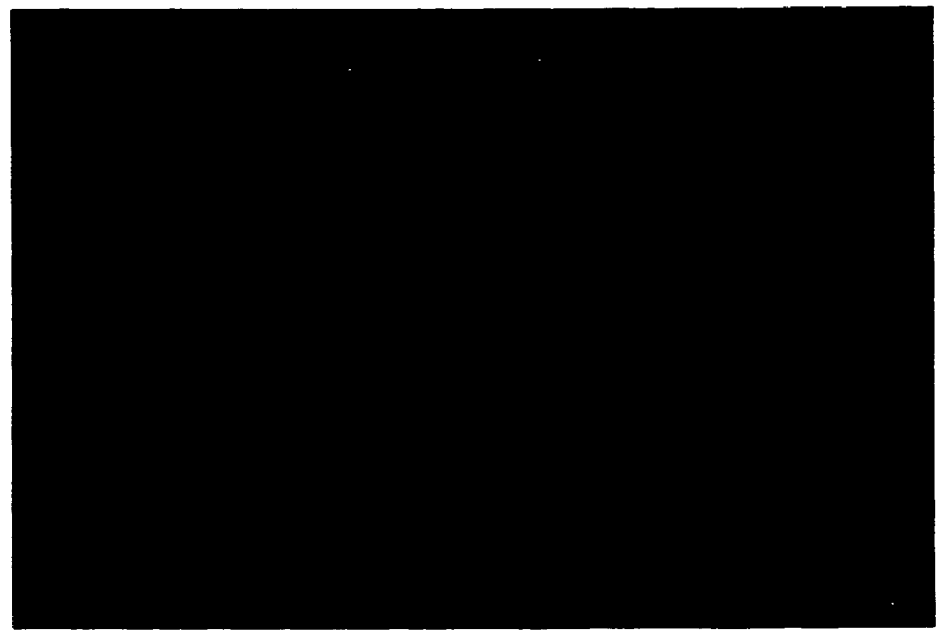

Transgene expression of the pEGFP-C1 plasmid was assessed by confocal microscopy of 20 μm cryosections of the fixed frozen tissue. The frozen sections were examined using the Olympus BX50/Biorad MRC 1000 confocal microscope with an Argon/Krypton laser. (Ex 488 nm, Em 515 for EGFP; Ex 568, Em 585 for rhodamine). Areas of tissue sections were imaged at 20× magnification. No image enhancements were used, but a color scale was applied for figure preparation. FIG. 14 shows a pair of fluorescent images from a tissue section taken from a pEGFP-C1 plasmid treated tumor. The lower panel shows red fluorescence from the rhodamine-labeled liposomes. The very high lipid signal (yellow) suggests that this section was near the sight of liposome injection. The top panel shows green fluorescence due to transgene expression. The signal from the expressed plasmid is near, but not coincidental to, the lipid signal, and appears to represent true expression of the plasmid in the tumor. FIG. 15 shows another pair of fluorescent images from a different tumor section with expressed EGFP. A fluorescent image pair from a cryosection of control tumor tissue is shown in FIG. 16. Weak, diffuse green fluorescence inherent in the tissue is visible in the top panel, but no area of intense fluorescence was found in any control tissue section. There was no red fluorescence in any control tumor section.

Example 17

Transfection of Mouse Muscle In Vivo

The transfection activity of NC12-DOPE/DOPC (70:30) liposomes encapsulating the pZeoSVLacZ plasmid was tested in vivo in mouse leg muscle. The liposomes were prepared as described in Example 3. Female DBA mice housed under standard conditions were used for this experiment. 50 μl liposomes containing the pZeoSVLacZ plasmid was injected directly into one rear leg muscle on day one. The injection site was near the fore thigh of the leg. The opposite leg received either 50 μl liposomes with pEGFP-C1 plasmid or no treatment. On day 2, 50 μl 20 mM sodium butyrate in HBSS was injected into the liposome treated legs. The mice were sacrificed on day 3 and the leg muscle excised as four sections: fore leg, hind leg, fore thigh and hind thigh. One half of the tissue from each section was frozen immediately in liquid propane, while the other half was fixed in 4% paraformaldehyde, cryoprotected with 30% sucrose then flash frozen in propane.

Figure 17:
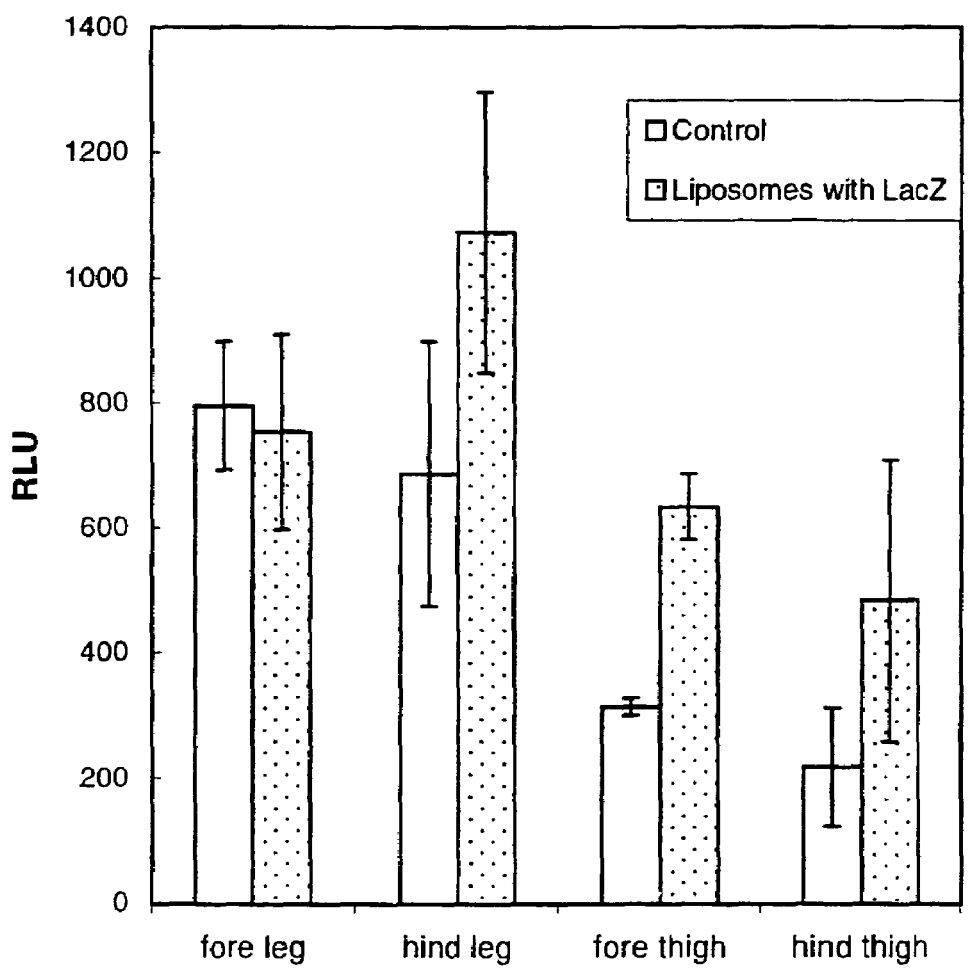

Transgene expression of the pZeoSVLacZ plasmid delivered via the N12-DOPE/DOPC (70:30) liposomes was assayed using the Clontech luminescent β-gal kit. Unfixed muscle was defrosted, cut into sections and homogenized as follows. 15 ml lysis buffer (9.15 ml $K_2HPO_4$, 0.85 ml $KH_2PO_4$, 20 μl Triton X100, 10 μl DTT) was added for each 1 mg wet tissue and hand homogenized for 5 min, then incubated at room temp for 20 min. The samples were then spun for 2 min at 14,000 rpm to pellet tissue debris. Aliquots of the supernatants were assayed for β-galactosidase activity as directed by Clontech. Light readings were measured after 60 min using a Berthold plate luminometer. Readings were averaged for different muscle sections of the same type. The results are shown in FIG. 17. A significant increase in β-galactosidase activity over control was found in muscle sections of the fore thigh. Slight increases were also noted in hind leg and hind thigh tissue.

These results demonstrate the in vivo transfection and transgene expression of pZeoSVLacZ plasmids when delivered to mouse muscle using the N12-DOPE/DOPC (70:30) liposome vector.

Example 18

Comparison of Transfection with Liposomal Condensed DNA and Cationic Lipoplex

Cationic Lipoplex Preparation:

Complexes of cationic lipids and helper lipids with plasmid DNA were prepared shortly before use. Lipofectin was purchased from Gibco BRL (Grand Island, N.Y.). For Lipofectin, the lipid alone was incubated in serum-free medium for approximately 45 minutes before complexation with DNA, as suggested by the manufacturer (Invitrogen). Equal volumes of 4 µg/ml DNA and 40 µg/ml lipid or equal volumes of 20 µg/ml DNA and 200 µg/ml lipid, all in serum free RPMI 1640 medium, were mixed and allowed to incubate for approximately 10-15 minutes before addition to wells of the tissue culture plates. $Ca^{2+}$ and $Mg^{2+}$ were adjusted to 1.2 mM and 0.8 mM final concentration, respectively, by addition of a concentrated stock just before addition of the lipoplexes to the cells. The ratio of lipid/DNA used for Lipofectin was based on an optimization comparing several ratios.

DC-Cholesterol/DOPE (4/6) complexes were formed essentially as previously described (Muldoon et al., *Biotechniques* 22, 162-167 (1997)) and used within 15 minutes. The optimized DNA/lipid ratio was used in all experiments, i.e. 4 µg/ml DNA was mixed with equal volume of 20 µg/ml lipid or 20 µg/ml DNA was mixed with equal volume of 100 µg/ml lipid.

All other complexes were formed using a set of cationic lipids or lipid mixtures from a single manufacturer (Invitrogen). These were prepared as suggested by the manufacturer at the 1× concentration and at the suggested lipid/DNA ratios.

Transfection assays were performed as described in Example 11.

Comparison to Cationic Lipoplexes:

The pelleted liposomes free of external DNA was used for direct comparison of transfection to cationic lipoplexes at equal DNA concentrations. These data are presented in Table 2 relative to the liposomal treatment (all data after incubation in sodium butyrate, a nontoxic activator of transgene expression (Tang et al., *Human Gene Therapy,* 8: 2117-2124 (1997); Wheeler et al., *Biochim Biophys Acta* 1280 (1996); Gruner et al., *Biochem* 24: 2833-2842 (1984)) and at physiological $Ca^{2+}$ and $Mg^{2+}$ levels; all data was normalized in terms of total intracellular esterase activity). In Table 2, the cell viability and transfection are taken as 1.0 for the N-C12-DOPE/DOPC liposomes, i.e numbers greater than 1.0 represent the factor by which either of these parameters is higher in the test system. The transfection activity of the N-C12-DOPE/DOPC (70:30) liposomes was generally in the range of that found for cationic lipoplexes under these conditions. Some lipoplexes gave considerably lower and some considerably higher activity. Lipoplexes containing 3β[N-(dimethylaminoethane)-carbamoyl]cholesterol and dioleoylphosphatidylethanolamine (DC-chol/DOPE) were particularly active. However, like all cationic lipoplexes, they were considerably more toxic than the liposomes to the particular cells used in these experiments, especially at the higher concentration. This could be observed in the lower calcein blue fluorescence after treatment with the lipoplexes (Table 2 data) as well as the microscopic observation of rounded and disrupted cells after treatment (data not shown). In several cases, the transfection efficiency of cationic lipoplexes actually decreased relative to liposomes at the higher concentration, probably as a result of their toxicity. No toxicity was observed with the liposomally encapsulated DNA. Interestingly, treatment with the liposomes commonly caused an increase in the final calcein blue fluorescence between 10 and 30 percent, possibly as a result of protection from the effects of the incubation in serum-free medium.

The importance of the relatively low toxicity of this liposomal plasmid DNA delivery system is not completely apparent in the tissue culture systems because the transfection efficiency reaches saturation at the relatively low levels of DNA used in the experiments above. However, the situation in vivo is expected to be much different. The large excess of nonspecific binding sites in vivo may necessitate the use of high levels of DNA and/or multiple injections for efficient expression in the target cells. There may be a limit to the use of cationic lipoplexes in this situation because of their toxicity.

Ovcar-3 cells were incubated with washed liposomal pellets (as in FIG. 10) or lipid complexes with equal amounts of pEGFP-C1 plasmid DNA for 3 hours in serum-free medium. All transfection procedures were as described in Example 11 and include adjustment of $Ca^{2+}$ and $Mg^{2+}$ levels to 1.2 and 0.8 mM, respectively.

TABLE 2

| Lipid/Mixture[a] | relative cell survival 2 µg/ml DNA[b] | s.d. | relative transfection 2 µg/ml DNA[b,c] | s.d. | relative cell survival 10 µg/ml DNA[b] | s.d. | relative transfection 10 µg/ml DNA[b,c] | s.d. |
|---|---|---|---|---|---|---|---|---|
| 1 | 0.631 | 0.078 | 0.619 | 0.203 | 0.313 | 0.011 | 0.942 | 0.222 |
| 2 | 0.651 | 0.084 | 0.987 | 0.216 | 0.401 | 0.009 | 0.794 | 0.207 |
| 3 | 0.639 | 0.059 | 0.833 | 0.272 | 0.352 | 0.006 | 1.186 | 0.267 |
| 4 | 0.739 | 0.078 | 1.655 | 0.382 | 0.297 | 0.017 | 1.327 | 0.395 |
| 5 | 0.618 | 0.070 | 0.096 | 0.064 | 0.460 | 0.011 | 0.091 | 0.024 |
| 6 | 0.704 | 0.077 | 1.050 | 0.224 | 0.366 | 0.008 | 1.182 | 0.266 |
| 7 | 0.660 | 0.069 | 0.096 | 0.030 | 0.431 | 0.008 | 0.802 | 0.231 |
| 8 (lipofectin) | 0.708 | 0.089 | 1.651 | 0.381 | 0.139 | 0.014 | 0.325 | 0.077 |

TABLE 2-continued

| Lipid/Mixture[a] | relative cell survival 2 μg/ml DNA[b] | s.d. | relative transfection 2 μg/ml DNA[b,c] | s.d. | relative cell survival 10 μg/ml DNA[b] | s.d. | relative transfection 10 μg/ml DNA[b,c] | s.d. |
|---|---|---|---|---|---|---|---|---|
| 9 (DC-chol/DOPE) | 1.095 | 0.101 | 4.930 | 0.991 | 0.383 | 0.032 | 2.451 | 0.627 |

[a]Cationic lipid complexes were prepared with the following lipids: #1 - 1:1 mixture of Tris-((2-glutaroyl-4-amino-N-dioctadecyl amine)-4'-(2,5-diaminopentanoyl-(2'',5''-diaminopropylethyl))amine, trifluoroacetate and 2-Amino-(2',2'-dimethyl)ethyl-methylphosphonic acid-O-octadecyl-(1'-heptadecyl) ester, trifluoroacetate (Pfx-1); #2 - 2,5-Diaminopentanoyl-glycyl-glycyl-N-octadecyl-(1'-heptadecyl) amide, trifluoroacetate (Pfx-2); #3 - 1:1 mixture of 2,5-Diaminopentanoyl-(2',3'-di-3-aminopropyl)-2-aminoacetyl-2-aminoacetyl-N-octadecyl-(1'-heptadecyl) amide, trifluoroacetate and DOPE (Pfx-3); #4 - 1:1 mixture of 2-Amino-(2',2'-dimethyl)ethyl-methylphosphonic acid-O-octadecyl-(1'-heptadecyl) ester, trifluoroacetate and 2,5-Diaminopentanoyl-2-aminoacetyl-N-dioctadecyl amide, trifluoride (Pfx-4); #5 - 1:1 mixture of 2,5-Diaminopentanoyl-(2,5-di-3-aminopropyl)-glutaroyl-N-octadecyl-(1'-heptadecyl) amide, trifluoroacetate and 2,5-Diaminopentanoyl-(2,2,5,5-tetra-3-aminopropyl)-glycyl-N-dioctadecyl amine, trifluoroacetate (Pfx-5); #6 - 1:1 mixture of 2,5-Diaminopentanoyl-(2,5-di-3-aminopropyl)-1,2-diaminoehtyl-O-octadecyl-(1'-heptadecyl)carbamic acid, trifluoride and DOPE (Pfx-7); #7 - Bis-(2,5-diaminopentanoyl-(2,5-di-3-aminopropyl)-cystyl-N-dioctadecyl amine))disulfide, trifluoroacetate (Pfx-8); #8 - lipofectin; #9 - DC-cholesterol/DOPE 4/6.
[b]Data is expressed relative to the N-acyl-PE-containing liposomes, taken as 1.0, i.e., the numbers represent the factor by which each lipoplex is more or less toxic or active. Data from more than one series of experiments was compared using lipid #2 as a standard.
[c]Transfection efficiency was measured by EGFP fluorescence as in FIG. 11 and corrected for total cell esterase activity as reflected in the total fluorescence of calcein blue (see Example 11).

One skilled in the art will readily appreciate the present invention is well adapted to carry out the objects and obtain the ends and advantages mentioned, as well as those inherent therein. The compounds, compositions, methods, procedures and techniques described herein are presented as representative of the preferred embodiments, or intended to be exemplary and not intended as limitations on the scope of the present invention. Changes therein and other uses will occur to those of skill in the art that are encompassed within the spirit of the appended claims.

What is claimed is:

1. A method of encapsulating a bioactive complex in a liposome which comprises the steps of:
    (a) dissolving at least one amphipathic lipid in one or more organic solvents;
    (b) combining a first aqueous suspension comprising a nucleic acid with the lipid containing organic solution of step (a) so as to form a water-in-oil emulsion comprising lipid stabilized water droplets containing the bioactive agent;
    (c) adding a second aqueous suspension comprising a polycation to the emulsion of step (b), so as to form a water-in-oil emulsion comprising the lipid stabilized water droplets of step (b) and lipid stabilized water droplets containing the polycation;
    (d) incubating the emulsion of step (c) to allow the polycation to contact the nucleic acid thereby forming a complex of the nucleic acid with the polycation within the lipid stabilized water droplets, wherein growth of said complex is limited by the diameter of the lipid stabilized water droplets; and
    (e) removing the organic solvent from the emulsion of step (d), so as to form liposomes comprising the complexed nucleic acid and the lipid,
    wherein the liposomes have number average sizes of about 50 to 300 nm, the liposomes encapsulate the complexed nucleic acid; and wherein the nucleic acid to lipid ratio is at least 0.5 μg nucleic acid per μmole of liposomal lipid.

2. A method of encapsulating a bioactive complex in a liposome which comprises the steps of:
    (a) dissolving at least one amphipathic lipid in one or more organic solvents;
    (b) combining a first aqueous suspension comprising a polycation with the lipid containing organic solution of step (a) so as to form a water-in-oil comprising the lipid stabilized water droplets containing the polycation;
    (c) adding a second aqueous suspension comprising a nucleic acid to the emulsion of step (b), so as to form a water-in-oil emulsion comprising the lipid stabilized water droplets of step (b) and lipid stabilized water droplets containing the nucleic acid;
    (d) incubating the emulsion of step (c) to allow the polycation to contact the nucleic acid thereby forming a complex of the nucleic acid with the polycation within the lipid stabilized water droplets, wherein growth of said complex is limited by the diameter of the lipid stabilized water droplets; and
    (e) removing the organic solvent from the emulsion of step (d), so as to form liposomes comprising the complexed nucleic acid and the lipid, wherein the liposomes have number average sizes of about 50 to 300 nm, wherein the liposomes encapsulate the complexed nucleic acid; and wherein the nucleic acid to lipid ratio is at least 0.5 μg nucleic acid per μmole of liposomal lipid.

3. The method of claim 1 or 2, wherein the nucleic acid is DNA or RNA.

4. The method of claim 3, wherein the nucleic acid is DNA.

5. The method of claim 1 or 2, wherein the polycation is selected from the group consisting of polylysine, a polyamine, hexammine cobalt, polyhistidine, and polyethyleneimine.

6. The method of claim 5, wherein the polyamine is selected from the group consisting of spermine and spermidine.

7. The method of claim 6, wherein the polyamine is spermine.

* * * * *